United States Patent [19]

Wissner

[11] 4,278,806
[45] Jul. 14, 1981

[54] 15-DEOXY-16-SUBSTITUTED-19-CHLORO-20-NOR PROSTANE DERIVATIVES OF THE E AND F SERIES

[75] Inventor: Allan Wissner, Ardsley, N.Y.

[73] Assignee: American Cyanamid Company, Stamford, Conn.

[21] Appl. No.: 46,725

[22] Filed: Jun. 7, 1979

[51] Int. Cl.³ .......................................... C07C 177/00
[52] U.S. Cl. .................................. 560/121; 260/408; 562/503; 424/305; 424/317
[58] Field of Search ...................... 560/121; 562/503; 260/408

[56] References Cited

U.S. PATENT DOCUMENTS 4,198,521  4/1980  Floyd .................................... 560/118

Primary Examiner—Robert Gerstl
Attorney, Agent, or Firm—Norton S. Johnson

[57] ABSTRACT

The invention disclosed herein relates to pharmacologically active prostaglandin derivatives of the E and F series wherein C-16 is substituted with hydrogen, methyl, vinyl or ethynyl and C-19 substituted with chloro and the β-chain consists of 7 carbon atoms.

14 Claims, No Drawings

15-DEOXY-16-SUBSTITUTED-19-CHLORO-20-NOR PROSTANE DERIVATIVES OF THE E AND F SERIES

BACKGROUND OF THE INVENTION (1) Field of the Invention

The present invention relates to 15-deoxy-16-hydroxy-16-hydrogen, methyl, vinyl or ethynyl, 19-chloro-20-nor prostaglandins, as well as the pharmaceutically acceptable, non-toxic lower alkyl esters and salts thereof, and to the intermediates and processes for producing such compounds.

(2) Description of the Prior Art

Prostaglandins have classically been described as chemically related 20 carbon chain hydroxy fatty acids having the basic skeleton of prostanoic acid:

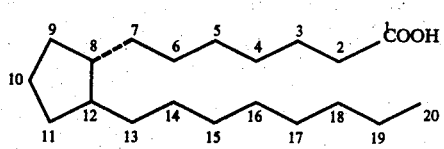

The prostaglandins having a hydroxyl group at the C-11 position and a keto group at the C-9 position are known as the PGE series, and those having a hydroxyl group in place of the keto group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the PGF$_1$ and PGE$_1$ series refer to prostanoic acids having a trans olefin bond at the C-13 position, while the PGF$_2$ and PGE$_2$ series refer to prostadienoic acids having a cis-olefin bond at the C-5 position and a trans olefin bond at the C-13 position. For a review on prostaglandins and the definition of primary prostaglandins, see, for example, P. Ramwell, *The Prostaglandins*, 1, pp. 5–22 (1973).

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axen et al, *Synthesis* Vol. 1, John Wiley and Sons Inc., New York, New York. 1973 and P. H. Bently, *Chem. Soc. Reviews*, 2, 29 (1973)].

The synthesis of prostaglandin analogs possessing a 3-oxa- or 11-deoxy-3-thia moiety have been described, among others in U.S. Pat. No. 3,873,607; U.S. Pat. No. 3,950,406; Netherlands Pat. No. 7305222-Q; U.S. Pat. No. 3,944,593; U.S. Pat. No. 3,931,289; and U.S. Pat. No. 3,936,487.

The synthesis of several prostaglandin analogs wherein the hydroxyl group at C-15 has been removed and a hydroxyl group has been introduced at C-16 has appeard [see for example, U.S. Pat. No. 3,950,406; *Prostaglandins*, Vol. 10, 733 (1975); *Tetrahedron Letters*, No. 48, 4217 (1975)].

Recently, reports have also appeared wherein the C-16 carbon bearing a hydroxyl group is substituted with a methyl group [see Pappo et al., *Tetrahedron Letters*, No. 4, 235 (1975); Collin et al., U.S. Pat. No. 3,965,143; and Belgium Pat. No. 827,127].

Also, a patent has recently appeared wherein the C-16 carbon bearing the hydroxyl group is substituted with vinyl, methylvinyl, and cyclopropyl (U.S. Pat. No. 4,061,670).

Prostaglandins which have been substituted with a chlorine, bromine or iodine atom include among others 19-chloro-15-hydroxy prostaglandins of the "1" series (U.S. Pat. Nos. 3,997,588, 4,041,050 and 4,056,562), 15-deoxy-15-halo-11-deoxy prostaglandins (U.S. Pat. No. 3,932,472) and 15-deoxy-20-chloro-prostaglandins of the "1" series (U.S. Pat. No. 3,884,953).

SUMMARY OF THE PRESENT INVENTION

In accordance with the present invention, disclosed are certain novel 15-deoxy-16-hydroxy-16-hydrogen, methyl vinyl and ethynyl-19-chloro-20-nor prostaglandin analogs represented by the following formula:

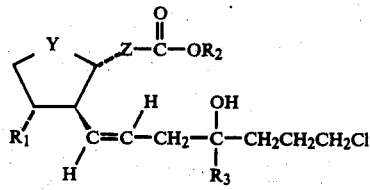

wherein Y is

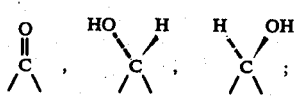

$R_1$ is selected from the group consisting of hydrogen and hydroxyl;

$R_2$ is selected from the group consisting of hydrogen and $C_1$-$C_6$ alkyl;

$R_3$ is selected from the group consisting of hydrogen methyl, vinyl and ethynyl.

Z is selected from the group consisting of a divalent moiety of the formulae: —(CH$_2$)$_n$—, —(CH$_2$)$_m$OCH$_2$—, —(CH$_2$)$_m$SCH$_2$—, and —(CH$_2$)CH=CH(CH$_2$)$_p$— wherein n is 5 to 7, preferably 6, m is 3 to 5, preferably 4 and p is 2 to 4, preferably 3; the racemic mixture thereof; and when $R_1$ is hydrogen, the pharmacologically acceptable salts thereof.

The dotted lines shown in the above formula and in the formulas below indicate that the substituents are in the α configuration, i.e., below the plane of the cyclopentane ring.

The double bond at C-13 in the compounds of the present invention has the same configuration as in natural prostaglandins of the PGE and PGF series, that is the trans configuration.

These novel compounds possess asymmetric centers and thus can be produced as racemic mixtures or as individual enantiomers. The racemic mixtures can be resolved if desired at appropriate stages by methods known to those skilled in the art, to obtain the respective individual enantiomers. It is to be understood that the racemic mixtures and the individual 8R-enantiomers are encompassed within the scope of the present invention.

When the compounds of the present invention are racemic mixtures, they are produced starting from racemates, while when the compounds of the invention are individual enantiomers the compounds are preferably obtained starting from the appropriate individual enantiomer.

Useful pharmacologically acceptable salts of the above formula, where $R_1$ is hydrogen, are those with pharmacologically acceptable metal cations, ammonium, amine cations or quaternary ammonium cations.

Preferred metal cations are those derived from the alkali metals, e.g., lithium, sodium and potassium, and from the alkaline earth metals, e.g., magnesium and calcium, although cationic forms of other metals, e.g. aluminum, zinc and iron, are within the scope of this invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenyethylamine, ethylenediamine, and arylipatic amines containing up to and including 18 carbon atoms, as well as heterocyclic amines, e.g., piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris-(hydroxymethyl)-aminomethane, N-phenylethanolamine, N-(p-tertamylphenyl)-diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The novel compounds of this invention can be prepared by a 1,4-conjugate-addition procedure involving treatment of the ether blocked cyclopentenone (17) with a lithio-cuprate reagent such as (14), (15) or (16) prepared as illustrated in Flowsheets A, B, C or D.

Although Flowsheets A and B exemplify the use of a trimethylsilyloxy protecting group, any protecting group which survives the conjugate addition reaction described by these tables and the example of this application may be employed. Suitable protecting groups therefore include tri($C_1$-$C_4$)alkylsilyl, or other acid labile protecting groups such astetrahydropyranyl, tetrahydrofuranyl, or other acetals. Moreover, with reference to the lithiocuprates of Flowsheets C and D (Structures (9) and (15)) in addition to the lithiocuprates described, the intermediates of structure (14) and (21) may also be employed.

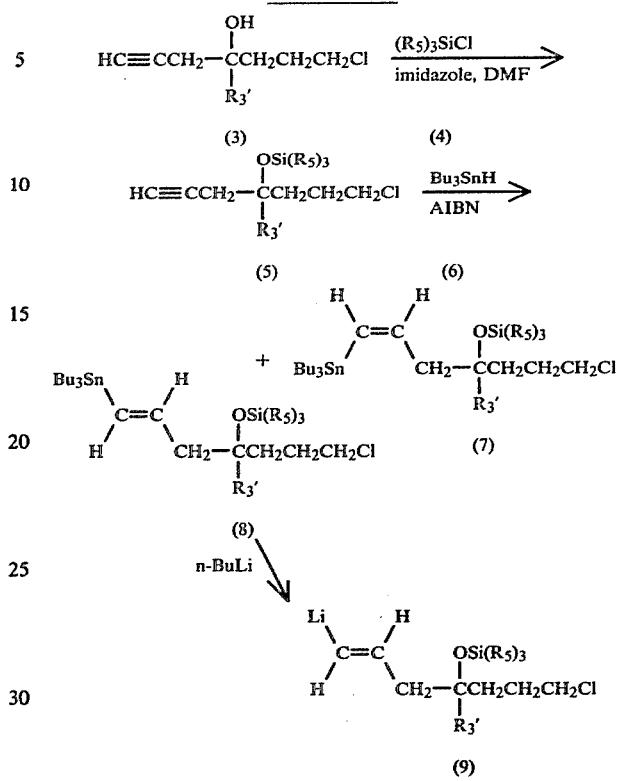

In accordance with Flowsheet A, wherein $R'_3$ is hydrogen, methyl, vinyl, and trimethylsilylethynyl, and $R_5$ is $C_1$-$C_4$ alkyl, treatment of the carbonyl compound (1) with propargylmagnesium bromide (2) in the presence of mercuric chloride provides the hydroxyalkyne (3). The hydroxy portion of (3) is protected with a trialkylsilyl group; triethylsilyl when $R'_3$ is hydrogen and trimethylsilyl when $R'_3$ is methyl, vinyl or trimethylsilylethynyl. The silyl ether (5) is heated with tri-n-butylstannane (6) in the presence of azobisisobutryonitrile (AIBN) to afford the trans-vinylstannane (7) which contains 10 to 20% of the corresponding cis-vinylstannane (8). Treatment of the vonylstannane (7) with n-butyl lithium at temperatures of −78° C. to −10° C. generates the vinyl lithium reagents (9).

The preparation of the carbonyl compound (11) wherein $R'_3$ is vinyl (7-chloro-hept-1-en-2-one) is shown in Flowsheet B. In accordance with Flowsheet B, 4-chlorobutrylchloride (10) is treated with vinyltrimethylsilane in the presence of aluminum trichloride at −20° C. to provide, after quenching with $NH_4Cl$ the vinylketone (11a). A similar sequence for the preparation of the trimethylsilylethynyl ketone (11b) is also illustrated in Flowsheet B by utilizing bis-trimethylsilylacetylene.

Flowsheet A

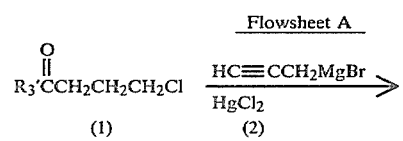

Flowsheet B

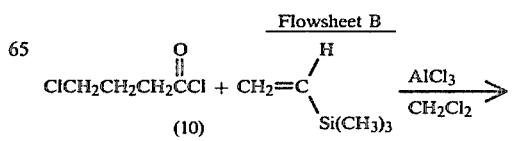

-continued
Flowsheet B

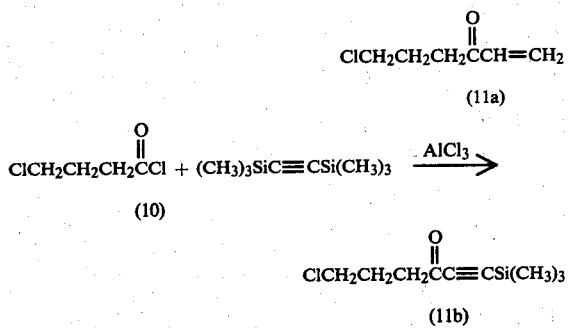

An alternate procedure to prepare precursors to the vinyl lithium reagent (9) is shown in Flowsheet C. In accordance with Flowsheet C, the silylether alkyne (5) is treated with diisoamylborane followed by treatment with trimethylamine oxide and then with $I_2$/NaOH, [Untch et al, *J. Amer. Chem. Soc.*, 94, 7827(1972)] to provide the 1-iodo-trans-alkenes (13). Treatment of the vinyliodide (13) with two equivalents of t-BuLi to generate the vinyllithium reagent (9).

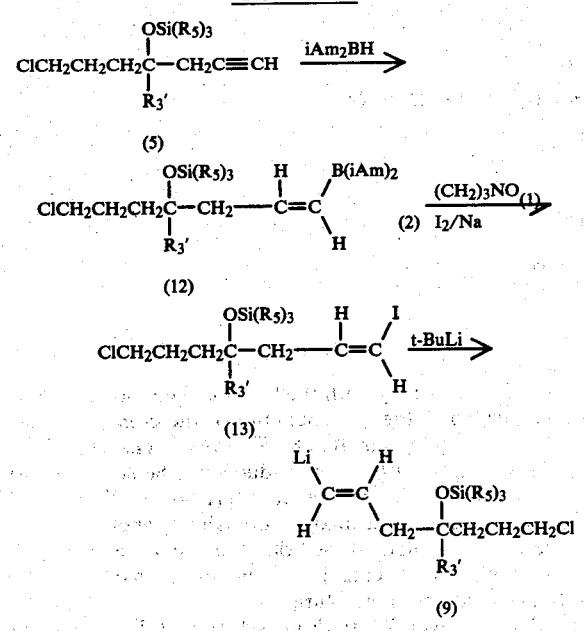

In accordance with Flowsheet D for the preparation of the asymmetrical lithio-cuprate (14) wherein $R_3$ is as previously defined or the like, a solution of one molar equivalent of copper (I)-1-alkyne, preferably copper (I)-1-pentyne in anhydrous tributylphosphine or HMPTA, preferably one to five molar equivalents, in ether is added to one molar equivalent of the aforementioned vinyl lithium solution cooled to about $-78°$ C. After about one hour at this temperature, a molar equivalent of the requisite cyclopentenone (17) is added. After several hours at $-30°$ C. to $-70°$ C. the reaction mixture is quenched with aqueous ammonium chloride solution and the blocked product (18) is isolated in the usual manner.

It is also possible to effect conjugate 1,4-addition with the asymmetrical lithio-cuprate (16) wherein $R_3$ is as previously defined derived from vinyl lithium and cuprous thiophenoxide. A solution of vinyl lithium (9) in ether at $-78°$ C. is reacted with an equimolar amount of a reagent prepared by admixture, in ether at a temperature of $0°$ C. to $-78°$ C., of equimolar amounts of cuprous thiophenoxide and copper (I) iodide tributlyphosphonium complex. After about 30 minutes at this temperature, the lithio-cuprate is treated with the requisite cyclopentenone (17) as described hereinabove for the conjuage addition with 1-alkynyl lithio-cuprate (14).

For the preparation of the symmetrical lithio-cuprate (15) wherein $R_4$ is as previously defined one molar equivalent of copper (I) iodide tributylphosphine complex, dissolved in anyhydrous ether, is added at about $-78°$ C. to two molar equivalents of the aforementioned vinyl lithium (9) solution cooled to $-78°$ C. After about one hour at this temperature, the lithio-cuprate (15) is treated with the requisite cyclopentenone (17) as described hereinabove for the conjuage addition with the 1-alkynyl lithio-cuprate (14)

The procedures for conjugate addition involving organocopper reagents are well known in the art, see for example C. J. Sih, et al, *J. Amer. Chem. Soc.*, 97, 865 (1975), which is incorporated by reference.

In the cases where $R'_1$=trimethylsilyloxy in cyclopentenone (17) the conjugate addition is performed at $-78°$ C. to $-40°$ C. The reaction is quenched by addition of an ether solution of acetic acid. Removal of blocking groups is then carried out as described in the reference above to provide the product (19) wherein $R_1$, $R_2$, and $R_3$ are as hereinabove.

In the instance wherein $R'_3$ is —C≡C—Si(CH$_3$)$_3$, generation of the 16—C≡CH function is accomplished by treatment with either KF in DMF or AgNO$_3$ followed by KCN.

The introduction of a racemic $\beta$-chain possessing the 16-hydroxy-16-hydrogen, methyl, vinyl or ethynyl-19-chloro-20-nor moiety provides a pair of prostaglandins epimeric at C-16. These two epimers may be separated into their upper (less polar) and lower (more polar) components by high-pressure liquid chromatography (HPLC) or by dry-column or preparative thin layer silica-gel chromatography.

If an optically active protected cyclopentenone such as (18) is utilized, then HPLC separation will provide the corresponding optically active nat. 9-oxo-11$\alpha$,16$\alpha$-dihydroxy- 16-hydrogen, methyl, vinyl or ethynyl -19-chloro-20-nor-and nat. 9-oxo-11$\alpha$,16$\beta$-dihydroxy-16-hydrogen, methyl, vinyl or ethynyl-19-chloro-20-nor-PGE enantiomers.

Flowsheet D

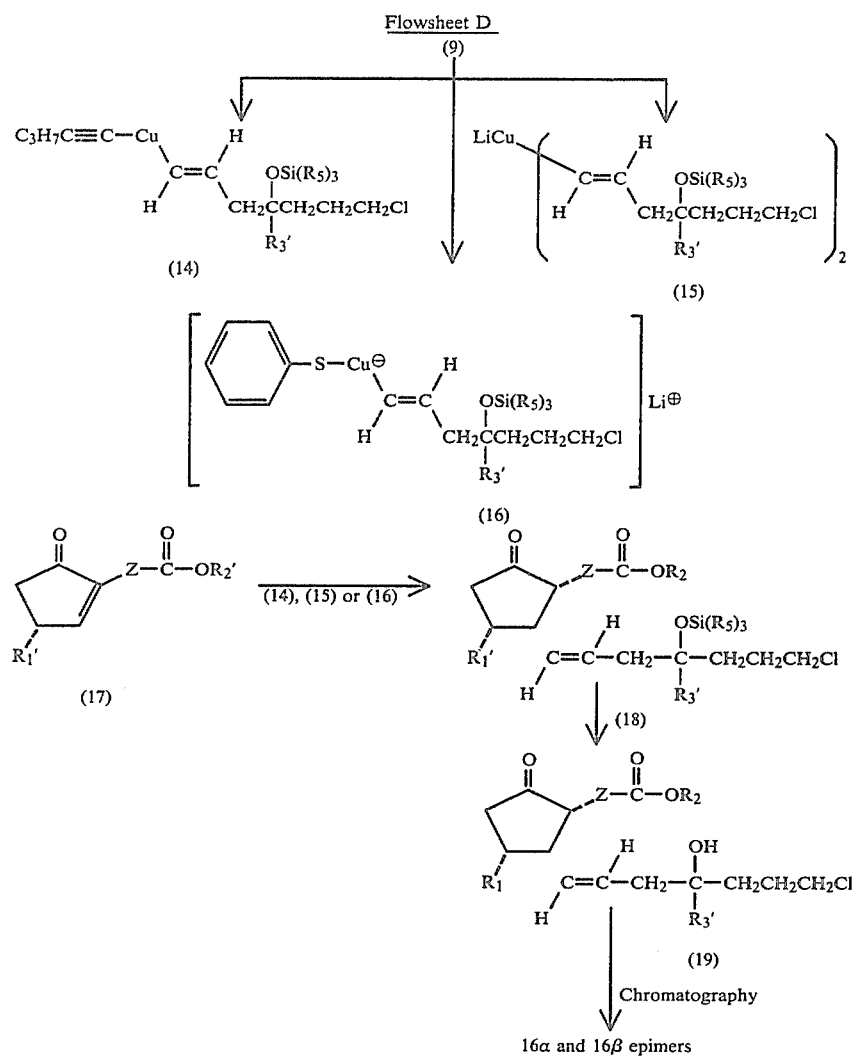

wherein R'$_2$ is lower alkyl C$_1$–C$_6$, tetrahydropyranyl, or trilower-(C$_1$–C$_3$) alkylsilyl;

R'$_1$ is hydrogen, tetrahydropyranyloxy, or trilower (C$_1$–C$_3$) alkylsilyloxy;

R$_1$, R$_2$, R$_3$, R'$_3$ are as hereinabove defined; Z is —(CH$_2$)$_n$—, —(CH$_2$)$_m$OCH$_2$—; —(CH$_2$)$_m$SCH$_2$—or

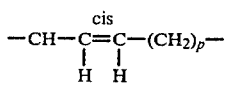

wherein m, n, and p are as previously defined.

All available evidence leads us to believe that the

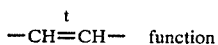

introduced by the cuprate process occupies a position trans to the 11-oxy function. Similarly, we are led to the conclusion that in the product (19) the two side-chains attached to C$_8$ and C$_{12}$ are trans to each other. However, we are not certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8ξ. In order to ensure a trans-relationship in (19) these products can be submitted to conditions known in the literature to equilibrate the cis-8-iso-PGE$_1$ to a mixture containing about 90% of the trans product. These conditions involve treatment with potassium acetate in aqueous methanol for 96 hours at room temperature.

The triloweralkylsilyloxy substituted lithio-cuprate reagents of type (20) and (21) and the trialkylstannyl precursors are novel and useful compounds which are also embraced by this invention. They may be defined by generic formulae

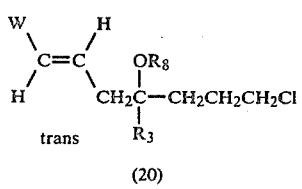

-continued $$\begin{bmatrix} R_9 \\ | \\ Cu^{\ominus} \\ | \\ C=C \\ / \quad \backslash \\ H \quad CH_2\overset{|}{\underset{R_3}{C}}-CH_2CH_2CH_2Cl \end{bmatrix} Li^+$$

trans (21)

wherein W is R-Sn wherein R is tri($C_1$–$C_6$)alkyl and preferably a tri-n-butyl group, or W is lithium; $R_8$ is tri($C_1$–$C_4$)alkylsilyl, preferably trimethylsilyl or other acid labile protecting groups such as tetrahydropyranyl, tetrahydrofuranyl or other acetals; $R_9$ is thiopenoxide, substituted thiophenoxide wherein the substituent may be $C_1C_4$ alkyl, $C_1C_4$alkoxy, $C_1C_3$dialkylamino or phenyl, or $R_9$ may be $C_3$–$C_4$alkyne or the identical vinyl moiety.

The cyclopentenones required for the preparation of the $E_1$, $E_2$, 3-oxa, and 11-deoxy-3-thia series have been described in the literature. The cyclopentenone for the preparation of 3-thia-11-hydroxy prostaglandins is described in Flowsheet E.

In accordance with Flowsheet E which is hereinbelow described, treatment of 2-furyl lithium (22) with a ω-chloroaldehyde (23) provides the chloroalcohol (24). Treatment of the chloroalcohol (24) with ethylmercaptoacetate furnishes the hydroxyester (25) which upon hydrolysis with sodium formate/formic acid provides the 3-hydroxy-cyclopentenone (26). Treatment of the cyclopentenone (26) with sulfuric acid provides the required 4-hydroxy-cyclopentenone (27) which after treatment with chlorotrimethylsilane provides the bis-silylated cyclopentenone (28).

Flowsheet E (furan)-Li + HC(=O)—(CH$_2$)$_4$—Cl → (furan)—CH(OH)—(CH$_2$)$_4$Cl
(22)      (23)                              (24)

HSCH$_2$CO$_2$C$_2$H$_5$ ↓

(furan)—CH(OH)—(CH$_2$)$_4$SCH$_2$COOC$_2$H$_5$
(25)

HCO$_2$Na/HCO$_2$H ↓

(cyclopentenone with OH and (CH$_2$)$_4$SCH$_2$COOC$_2$H$_5$)
(26)

H$_2$SO$_4$ ↓

HO—(cyclopentenone)—(CH$_2$)$_4$SCH$_2$COOH
(27)

(CH$_3$)$_3$SiCl →

-continued
Flowsheet E $$(CH_3)_3SiO-\text{(cyclopentenone)}-(CH_2)_4SCH_2COOSi(CH_3)_3$$
(28)

In accordance with Flowsheet F, when the 11-hydroxy or 11-oxy derivatives are treated with dilute acid, it is possible to effect elimination and the formation of the corresponding $\Delta^{10}$ derivatives (29) of the prostaglandin A-type. A preferred procedure involves treatment in tetrahydrofuran:water (2:1) solvent 0.5 N in HCL for about 30 hours at ambient temperature. Under these conditions a tetrahydropyranyl or trialkylsilyl ester or ether will undergo hydrolysis.

FLOWSHEET F

(18) or (19) →

$$\text{(cyclopentenone with } Z-C(=O)-OR_1 \text{ and } C=C-CH_2-C(H)(OH)-CH_2CH_2CH_2Cl, R_3\text{)}$$
(29)

The prostaglandin carboxylic acids of this invention can be readily converted to the various alkyl esters of this invention by treatment in the usual manner with the appropriate diazoalkane. The preparation of diazoalkanes by various procedures are well described in the art. See for example C. D. Gutsche, *Organic Reactions*, VIII, 389 (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsily, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydrides are then treated with the appropriate alcohol to give the derivatized products. [For a pertinent literature analogy see *Prostaglandins*, 4, 768 (1973).]

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279). A third procedure involves the use of dicyclohexylcarbodiimide in the usual manner;

for a pertinent literature analogy see German Offen. 2,365,205; *Chem. Abst.*, 81 120098g (1974).

The esterified alcohol derivatives of this invention are also prepared in the usual manner by procedures well known in the art from the appropriate alkanoic acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19–27 (August 1973) as well as references cited therein. Additional information, concerning high speed liquid chromatography and the instruments necessary for its application, is available from Waters Associate Inc., Maple Street, Milford, Mass.]

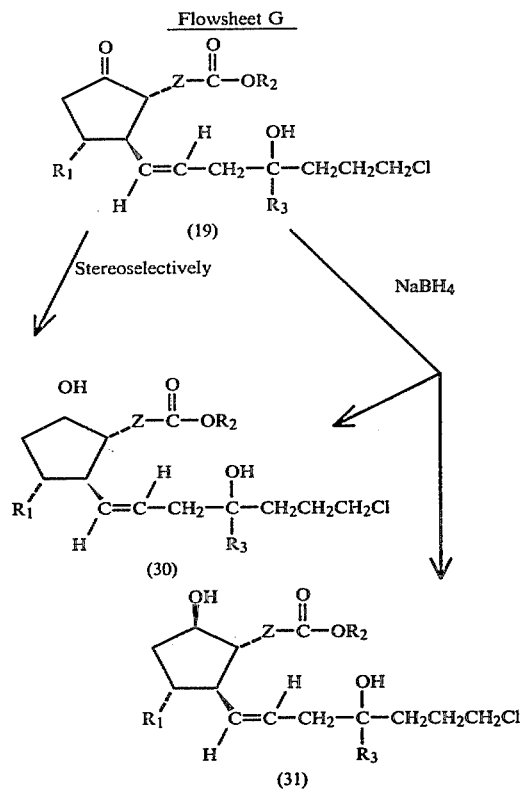

In accordance with Flowsheet G treatment of a prostaglandin of the E series (9-oxo) (19) with a carbonyl reducing reagent such as sodium borohydride provides a mixture of the corresponding PGFα(9β-hydroxy) (30) and PGFα (9β-hydroxy) (31) analogs. These two epimeric alcohols are readily separated by silica gel chromatography.

If one utilized the individual 16α-hydroxy or 16β-hydroxy E starting material after separating the 9β product by silica gel chromatography, the isolated products are the 9α,16α-dihydroxy and 9α,16β-dihydroxy derivatives respectively.

Use of a stereoselective reagent such as lithiumperhydro-9b-boraphenalylhydride [H. C. Brown and W. C. Dickason, *J.A.C.S.*, 92, 709 (1970)] or lithium tri-sec-butylborohydride [H. C. Brown and S. Krishnamurthy, Ibid, 94, 7159 (1972)] provides the PGFα product as the selective species.

Likewise, utilization of either the individual 16α- or 16β-hydroxy E compounds affords the corresponding 9α,16α-di-hydroxy and 9α,16β-dihydroxy prostaglandins of this invention respectively.

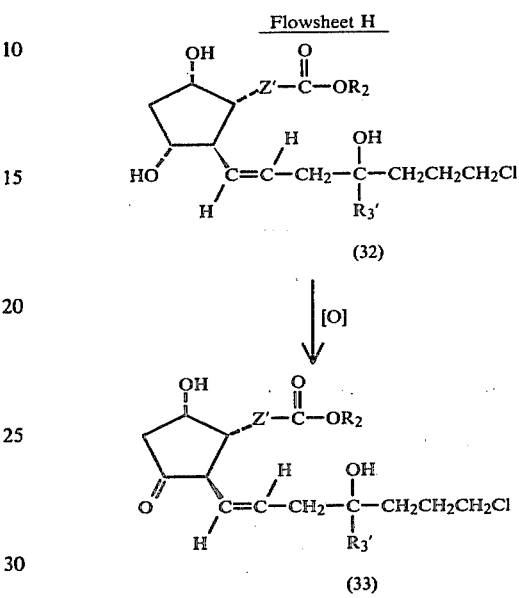

In accordance with Flowsheet H when 11α-hydroxy-PGF2α congeners such as (32) wherein R'₃ is methyl, vinyl or ethynyl are treated with an oxidizing reagent such as Jones Reagant, or pyridinium chlorochromate provides a selective oxidation to give the corresponding PGD derivative (9α-hydroxy-11-keto) (33) which is isolated after chromatographic purification.

If one utilized the individual 16α-hydroxy or 16β-hydroxy PGFα derivative of (32), then the corresponding 9α,16β-dihydroxy-11-oxo-prostaglandins are isolated, respectively.

In the following formulae Z is as hereinabove defined.

The 4-hydroxycyclopentenone racemates may be resolved into their component enantiomers (35) and (36) wherein Z is as hereinabove defined by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-α-methylpentanoic acid hydrochloride (to give (34)), (R)-2-aminoxy-3,3-dimethylbutyric acid hydrochloride, and 4α-methylbenzyl semicarbazide. After separation of the diastereomeric derivatives, reconstitution of the keto function provides the individual 4-hydroxycyclopentenone enantiomers (35) and (36). A useful procedure for the resolution of a 4-hydroxycylopentenone racemate via an oxime such as (34) is described in the art [R. Pappo, P. Collins and C. Jung, *Tetrahedron Letters*, 943 (1973)]. The resolution of the hydroxycyclopenteone (35) wherein Z is

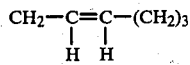

is described by Bruhn et al, *Tetrahedron Letters*, 235 (1976).

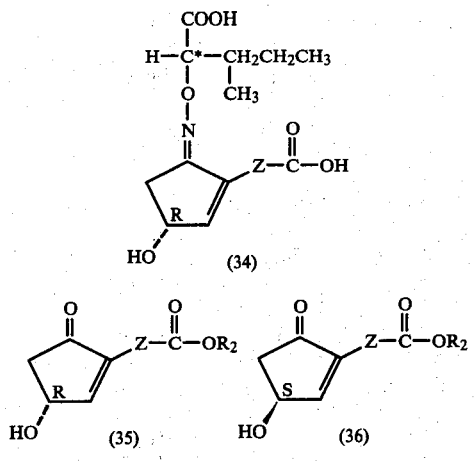

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various nonsteroidal anti-inflammatory agents (e.g., indomethacin, aspirin, and phenylbutazone), bronchodilators, anti-inflammatory agents, abortifacients, agents for the induction of labor, agents for the induction of menses, fertility-controlling agents, oestrus regulators for use in animal husbandry with cattle and other domestic animals and central nervous system regulatory agents. Certain of the novel compounds of this invention possess utility as intermediates for the preparation of the other novel compounds of this invention.

The novel compounds of this invention possess the pharmacological activity described below as associated with the appropriate above-described prostaglandin types.

The known PGE, PGF$_\alpha$, PGF$_\beta$, PGA and PGD compounds are all potent in causing multiple biological responses even at low doses. For example, PGE$_1$, PGE$_2$, PGA$_1$ and PGA$_2$ are extremely potent in causing vasodepression and smooth muscle stimulation, and also are potent as antilipolytic agents. For example, the 11-deoxy-PGE compounds of this invention are selective in that they are at most relatively weak stimulants of smooth muscle. A further advantage of these novel compounds should be in their increased stabilities and lengthened shelf-lives.

Therefore, each of these novel prostaglandin analogs of this invention should be more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

Another advantage of the novel compounds of this invention, compared with the known prostaglandins, is that these novel compounds are administered effectively orally, sublingually, intravaginally, buccally, or rectally, in addition to the usual intravenous, instramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

PGE$_1$, PGE$_2$, PGE$_3$, dihydro-PGE$_1$, PGF$_\alpha$, PGF$_\beta$ and PGA compounds, their esters and pharmacologically acceptable salts, are extremely potent in causing various biological responses. For that reason, these compounds are useful for pharmacological purposes. See, for example, Bergstrome, et al., *Pharmacol. Rev.*, 20, 1 (1968), and references cited herein. A few of these biological responses are systemic arterial blood pressure lowering in the case of the PGA and PGE compounds as measured, for example, in anesthetized (sodium phenobarbital) pentolinium-treated rats with indwelling aortic and right heart cannulas; pressor activity, similarly measured, for the PGF compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of PGE compounds, as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen, and in the case of the PGE and PGA compounds, stimulation of epidermal proliferation and keratinization, as shown when they are applied in culture to embryonic chick and rat skin segments.

Because of these biological responses, these known prostaglandins are useful to study, prevent, control, or alleviate a wide variety of disease and undesirable physiological conditions in birds and mammals including humans, useful domestic animals, pets, and zoological specimens, and in laboratory animals, e.g., mice, rats, rabbits, and monkeys.

For example, these compounds are useful in mammals, including man, as nasal decongestants. For this purpose, the compounds are used in a dose range of about 10 mg to about 10 mg per ml of a pharmacologically suitable liquid vehicle or as an aerosol spray, both for topical application.

PGA, PGF$_\beta$ and PGE compounds are useful as hypotensive agents to reduce blood pressure in mammals including man. For this purpose, the PGF$_\beta$ compounds are administered by intravenous infusion at the rate of about 0.01 mg to about 40 mg per Kg of body weight per minute, or in a single dosage or multiple doses of about 25 mg to 2500 mg per Kg of body weight total per day. The PGE and PGA compounds are administered by intravenous infusion at the rate of about 0.01 to about 50 mg per Kg of body weight per minute, or in a single dose or multiple doses of about 25 to 2500 mg per Kg of body weight total per day.

The PGE, $PGF_\alpha$ and $PGF_\beta$ compounds are useful in place of oxytocin to induce labor in pregnant female animals, including humans, cows, sheep and pigs, at or near term or in pregnant animals with intrauterine death of the fetus from about 20 weeks to term. For this purpose, the PGF compound is infused intravenously at a dose of 0.01 mg to 50 mg per Kg of body weight per minute until or near the termination of the second stage of labor, i.e., expulsion of the fetus. Similarly, the PGE compound is infused intravenously a a dose of 0.01 to 50 mg per Kg of body weight per minute until or near the expulsion of the fetus. These compounds are especially useful when the female is one or more weeks postmature and natural labor has not started, or 12 to 60 hours after the membranes have ruptured and natural labor has not yet started.

The PGE, $PGF_\alpha$ and $PFG_\beta$ compounds are useful for controlling the reproductive cycle in ovulating female mammals, including humans and other animals. For that purpose, $PGF_{2\alpha}$, for example, is administered systemically at a dose level in the range of 0.01 mg to about 20 mg per Kg of body weight, advantageously during a span of time starting approximately at the time of ovulation and ending approximately at the time of menses or just prior to menses. Likewise, a PGE compound is administered in the same fashion at a dose level of 0.01 mg to about 50 mg per Kg of body weight. Additionally, expulsion of an embryo or fetus is accomplished by similar administration of the compound during the first third or the second third of the normal mammalian gestation period. Accordingly, such compounds are useful as abortifacients. They are also useful for induction of menses during approximately the first two weeks of a missed menstrual period and thus, are useful as contraceptive anti-fertility agents.

$11\alpha$-hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators for example, to relieve the symptoms of paralytic ileus, to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 mg per Kg of body weight per minute until the desired effect is obtained. Subsequent doses are given by intravenous, subcutaneous, or intramuscular injection or infusion during puerperium in the range of 0.01 to 2 mg per Kg of body weight per day, the exact dose depending on the age, weight, and condition of the patient or animal.

The novel PGA, PGE and $PGF_\beta$ of this invention are also useful as bronchodilators for the treatment of asthma and chronic bronchitis. As such they may be conveniently administered by inhalation of aerosol sprays prepared in a dose range of about 10 µg to about 10 mg/ml of a pharmacologically suitable liquid vehicle. Relative to the natural prostaglandins, the PGA and PGE compounds in particular have the significant advantage of inducing prolonged effects.

The PGE and PGA compounds are also useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 0.1 mg to about 500 mg per Kg of body weight per minute, or in a total daily dose by injection or infusion in the range of about 0.1 to about 20 mg per Kg of body weight per day, the exact dose depending on the age, weight, and condition of the patient or animal, and on the frequency and route of administration. These compounds may also be useful in conjunction with various non-steroidal anti-inflammatory agents, such as aspirin, phenylbutazone, indomethacin and the like, to minimize the well-known ulcerogenic effects of the latter.

The PGE and PGA compounds also stimulate epidermal proliferation and keratinization, and in such a capacity are useful to promote and accelerate healing of skin which has been damaged, for example, by burns, wounds, abrasions or surgery. The nasopressor action of the PGA compounds makes them particularly useful in speeding the adherence and growth of skin autografts, especially small, deep (Davies) grafts which are intended to cover skinless areas by subsequent outward growth rather than initially, and in retarding rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion cream, or ointment in combination with the usual pharamaceutically acceptable diluents. In some instances, when there is substantial fluid loss as in the case of extensive burns or skin loss due to other causes, systemic administration of PGE is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Illustrative of a wet dressing for topical application to second and/or third degree burns of skin area 5 to 25 square centimeters is the use of an isotonic aqueous solution containing one to 500 mg/ml of the PGA compound or several times that concentration of the PGE compound. Especially for topical use, these prostaglandins are useful in combination with antibiotics such as gentamycin, neomycin, polymyxin B, bacitracin, spectinomycin, and oxytetracycline; with other antibacterials such as mafenide hydrochloride, sulfadiazine, furazolium chloride, and nitrofurazone; and with corticoid steroids, such as hydrocortisone, prednisolone, methylprednisolone, and fluoroprednisolone; each of those being used in the combination at the usual concentration suitable for its use alone.

The PGA compounds and derivatives and salts thereof increase the flow of blood in the mammalian kidney, thereby increasing the volume and electrolyte content of the urine. For that reason, PGA compounds are useful in managing cases of renal disfunction, especially in cases of severely impaired renal blood flow, for example, the hepatorena syndrome and early kidney transplant rejection. In case of excessive or inappropriate antidiuretic hormone ADH vasopressin secretion, the diuretic effect of these compounds is even greater. In anephretic states, the vasopressin action of these compounds is especially useful.

The PGE compounds of this invention are also useful as topical vasodilators.

The $PGE_1$ compounds of this invention are useful whenever it is desired to inhibit platelet aggregation, to reduce the adhesive character of platelets, and to remove or prevent the formation of thrombi in mammals including man, rabbits, and rats. For example, these compounds are useful to treat and prevent myocardial infarcts and post-operative thrombosis. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.005 to about 20 mg per Kg of body weight per day are used, the exact dose depending on the age, weight, and condition of the patient or animal, and on the frequency and route of administration.

It is well known that platelet aggregation inhibitors may be useful as anti-thrombotic drugs. Inhibition of platelet aggregation can be conveniently measured in vitro by monitoring changes in optical density and/or light transmission in platelet rich plasma upon addition of suitable aggregating agents such as adenosine diphosphate, epinephrine, thrombin or collagen. Alternatively, platelet aggregation can be measured in vitro using platelet rich plasma obtained at various time intervals from animals given inhibitors by an oral or parenteral route.

The PGE compounds of the present invention exhibit the ability to inhibit platelet aggregation in vitro when tested by the following procedure.

Human protein rich plasma is incubated with modified Tyrode's solution in a proportion of 40–50% human protein rich plasma. The test compounds are added at varying concentrations and after 5 minutes incubation, an aggregating agent such as adenosine diphosphate or collagen is added. The change in optical density (light transmission) is monitored by eye and inhbition is recorded as a (−) or lack of inhibition is recorded as a (+). Test compounds are considered active if they inhibit adenosine diphosphate or collagen induced aggregation at a concentration of 0.025 mg/ml or less within 5–10 minutes.

The PGE compounds of this invention also have bronchodilator activity as determined in a test using dogs anesthetized, artificially ventilated and submitted to a continuous respiratory spasm induced by pilocarpine procedure.

Mongrel dogs of either sex weighing between 5 and 10 kg are used. They are premedicated with morphine HCl by subcutaneous injection at 1.5 mg/Kg. An intravenous perfusion of 5% (W/V) chloralose is started ½ hour after the morphine injection in such a way that 60 mg/Kg are administered within 15 minutes. After completion, a continuous perfusion of 10 mg/Kg/hour is maintained throughout the experiment. The dogs are artificially ventilated by means of a Starling pump at a rate of 20 breaths/minute. The volume is adjusted according to the weight of the animal. [Kleinman and Radford, *J. Appl. Physiol.*, 19, 360 (1964)]. All the measurements are made with the dogs positioned supine in a heated, V-shaped table. Curarization is obtained by succinylcholine chloride using a starting injection of 3 mg/Kg lasting 3 minutes, followed by a continuous perfusion of 0.1 mg/Kg/minute.

The respiratory spasm is induced by a starting injection of 400 μg/Kg of pilocarpine HCl lasting 5 minutes. An increase ir decrease in the dose of pilocarpine HCl may occur as a function of the observed effect on the airway's resistance. A 15 minute delay is observed before the start of a continuous perfusion of pilocarpine HCl at a dose of 4 μg/Kg/minute to maintain a constant spasm during the test.

A metallic cannula is inserted and fixed, after tracheotomy, into the upper part of the trachea. The two cephalic veins and the two femoral veins are catheterized to inject the various agents. The femoral artery is catheterized to measure the systemic blood pressure. An esophageal balloon (11 cm × 2.5 cm) is inserted into the lower third of the oesophagus to measure the endothoracic pressure. The measurement of air flow is made with a Fleish pneumotachograph connected to the tracheal tube.

The transpulmonary pressure is measured as follows: The tracheal cannula is equipped with a stainless steel axial tube (1.5 mm) which is closed at its distal end and projected 2.5 cm beyond the end of the cannula. Three holes with a diameter of one mm are pierced on this latter segment. This tube, which is used to measure the tracheal pressure, is connected to one of the two chambers of a Sanborn 267 B/C differential transducer. The other chamber is connected to the esophageal ballon by means of a polyethylene catheter of the same length and characteristics as the balloon's.

The airflow is measured from the Fleish pneumotachograph by means of a Sanborn 270 differential transducer.

The tidal volume is obtained by electronic integration of the flow signal using an R.C. integrator.

The systemic and pulmonary blood pressures are gauged by means of a Sanborn 267 B/C or 1280B pressure transducer.

An electrocardiogram is taken in lead 2. Its use is to monitor a cardiac rate-meter.

All these parameters are recorded on a Sanborn polygraph. The transpulmonary pressure and the tidal volume are also displayed as rectangular coordinates on an oscilloscope.

The airway's resistance, expressed in cm of water/liter/second, is measured by subtracting from the electrical equivalent of the transpulmonary pressure, a voltage proportional to the flow so as to synchronize the pressure and volume signals on the oscilloscope [Mead and Whittenberger, *J. Appl. Physiol.*, 5, 799 (1953)].

The value of the pulmonary elastance, expressed in cm of water/liter, is obtained by means of the same principle, i.e., an electrical signal proportioned to the volume is subtracted from the transpulmonary pressure signal, in order to optimize the pressure-flow loop on the oscilloscope.

The details of this method are described by Lulling, et al. [*Med. Pharmacol. Exp.*, 16, 481 (1967)].

The computing operations are carried out with an analogical computer which allows the direct reading, cycle to cycle, of the values of resistance and elastance.

The test compounds are administered by an Aerosol® route. The micronebulizer of a Bird Mark 7 respirator is fitted on the metallic cannula just after the pneumotachograph. The "puff" of the test compound, in Aerosol ® is driven by a 2 Kg/cm$_2$ pressure, allowed into the microneblizer just during one inspiration cycle. The microneblizer is fitted on the respiratory tube only during the "puff." It is weighed just before and just after administration to determine the amount of test compound administered. Approximately 50 mg of the solution is administered to each dog. In accordance with the Pilocarpine Assay described herein, the compounds of this invention should exhibit bronchodilator activity.

The bronchodilator activity for representative compounds of this invention was determined in Guinea-Pigs against bronchospasms elicited by intravenous injections of serotonin, histamine, and acetylcholine, by the Konzett procedure the details of which are those discussed by J. Lulling, P Lievens, F. El Sayed and J. Prignot, *Arzeimittel-Forschung* 18, 995 (1968).

In the table which follows, bronchodilator activity for representative compounds of the invention against spasmogenic agents serotonin, histamine, and acetylcholine is expressed as an ED$_{50}$ determined from the results obtained with three logarithmic cumulative intravenous doses.

| | KONZETT DATA | | |
|---|---|---|---|
| | ED$_{50}$ (g/Kg) | | |
| COMPOUND | SEROTONIN | HISTAMINE | ACETYL-CHOLINE |
| dl 11α,16-dehydroxy-9-oxo-19-chloro-20-nor-5-cis,13-trans prostadienoic acid | 4.65 × 10$^{-6}$ | 4.4 × 10$^{-6}$ | 6.8 × 10$^{-6}$ |

Reference Example 1

7-Chloro-4-hydroxy-4-methyl-1-heptyne

To a mixture of 6.69 g. of magnesium in 20 ml. of ether under argon, is added 0.1 g. of mercuric chloride and 0.1 g. of dibromoethane. The mixture is stirred for 10 minutes and 0.5 ml. of propargyl bromide is added. A 50 ml. portion of ether is added, followed by a solution of 30 g. of 5-chloro-2-pentanone and 32.55 g. of propargyl bromide in 45 ml. of ether with stirring, at a rate to maintain vigorous reflux. The mixture is stirred an additional 15 minutes, cooled to −5° C. and an ice cold saturated solution of ammonium chloride is added dropwise. The ether layer is decanted and filtered. The solids are washed with ether which is also filtered. The combined ether filtrates are washed with water, dried over magnesium sulfate and the solvent removed giving the product as an orange oil.

Reference Example 2

7-Chloro-4-methyl-4-trimethylsilyloxy-1-heptyne

To a solution of 7-chloro-4-hydroxy-4-methyl-1-heptyne in 80 ml. of dimethylformamide at 0° C., is added 43.8 g. (0.644 moles) of imidazole and 35.02 g. (0.322 moles) of chlorotrimethylsilane. The mixture is stirred at room temperature for 45 minutes, poured into water and extracted with hexane. The hexane solution is washed with dilute sodium bicarbonate solution, dried over magnesium sulfate and the solvent removed leaving an orange liquid. This liquid is distilled giving the desired product in the fraction boiling at 83°–88° C., 1.5 mm. as a colorless liquid.

Reference Example 3

E/Z-1-Tri-n-butylstannyl-7-chloro-4-methyl-4-trimethylsilyloxy-1-heptyne

A stirred mixture of 15 g. of 7-chloro-4-methyl-4-trimethylsilyloxy-1-heptyne, 18.92 g. of tri-n-butylstannane 80 mg. of azobisisobutyrylnitrile, under argon is placed in a bath at 100° C. The mixture is heated at 140° C. for one hour. Excess tri-n-butylstannane is distilled off under vacuum. The residue is distilled via a Kugelrohr (130°–135° C., 0.03 mm.) to give the desired product as a colorless liquid.

Reference Example 4

9-oxo-11α,16-dihydroxy-16-methyl-19-chloro-20-nor-5-cis,13-trans-prostadienoic acid To a solution of 8.85 g. of E/Z-1-tri-n-butylstannyl-4-methyl-4-trimethylsilyloxy-7-chloro-1-heptyne in 10 ml. of tetrahydrofuran is added 7.71 ml. of 2.2 M. n-butyllithium under argon at −78° C. The solution is stirred at −20° to −15° C. for 2.5 hours and then cooled to −78° C. A solution of 2.23 g. of pentynyl copper and 6.2 g. of tributylphosphine in 50 ml. of ether is added. After 45 minutes a solution of 3.5 g. of 2-(6-carbotrimethylsiloxyhex-2-cis-enyl)-4-trimethylsiloxycyclopent-2-en-1-one in 3 ml. of ether is added. The mixture is stirred one hour at −40° C., ½ hour at −40° to −20° C. and 10 minutes at −20° C. The mixture is recooled to −30° C. and 3 ml. of acetic acid followed by saturated ammonium chloride solution are added. The mixture is extracted with ether and the ether solution is washed with dilute hydrochloric acid. The ether is removed and the residue is mixed with 70 ml. of acetic acid:- tetrahydrofuran:water (4:2:1) and stirred at 40° C. for 45 minutes. The solvents are removed and the residue is dissolved in ethyl acetate. The solution is washed with ammonium chloride solution, dried over magnesium sulfate and the solvent removed, giving a two phase oil. This oil is chromatographed on silica gel, eluting with ether-1% acetic acid to give the desired product.

Reference Example 5

E-7-Chloro-1-iodo-4-methyl-4-trimethylsilyloxy-1-heptane

To a solution of 9.1 g. of sodium borohydride and 44 g. of 2-methyl-2-butene in 390 ml. of tetrahydrofuran, at 0° C. under argon, is added dropwise with stirring 44.56 g. of boron trifluoride etherate. The mixture is stirred 1.5 hour at 0° C., 0.5 hour at room temperature, recooled to 0° C. and a mixture of 43 g. of 7-chloro-4-methyl-4-trimethylsilyloxy-1-heptene in 60 ml. of tetrahydrofuran is added over 10 minutes. The mixture is stirred 2 hours at room temperature, then 81.8 g. of trimethylamine oxide is added portionwise over 15 minutes at 0° C. The mixture is stirred 1.5 hour at room temperature, then filtered through Celite. To the filtrate is added simultaneously, a solution of 413.7 g. of sodium hydroxide in 2 liters of water and a solution of 211 g. of iodine in 350 ml. of tetrahydrofuran. The solution is stirred vigorously for 0.5 hour, the organic layer is separated and the aqueous layer is extracted with hexane. Most of the tetrahydrofuran is removed from the initial organic layer and it is combined with the hexane extract. The combined solution is washed twice with saturated sodium thiosulfate solution, brine, dried over magnesium sulfate and filtered through a pad of silica gel. The residue is distilled via a Kugelrohr at 115°–120° C., 0.15 mm. giving the desired product as a yellow oil.

Reference Example 6

Preparation and separation of 9α,11α,16-Trihydroxy-19-chloro-20-nor-5-cis,13-trans-prostadienoic acid and 9β,11α,16-trihydroxy-19-chloro-20-nor-5-cis,13-transprostadienoic acid To a stirred, ice-cold solution of 9-oxo-11α,16-dihydroxy-19-choro-20-nor-5-cis,13-trans-prostadienoic acid in ethanol is added excess sodium borohydride in small portions during 1 minute. The mixture is stirred at 0° C. for 5 minutes and at ambient temperature for 1.5 hours. The bulk of the ethanol is evaporated in vacuo at room temperature and the residue is partitioned with cold, very dilute, hydrochloric acid and ethyl acetate. The organic phase is evaporated and washed with water and brine, and dried over magnesium sulfate and concentrated in vacuo.

The residue is subjected to silica-gel chromatography to give: first eluted-9α,11α,16-trihydroxy-19-chloro-20-nor-5-cis,13-trans-prostadienoic acid followed by 9β,11α,16-trihydroxy-19-chloro-20-nor-5-cis,13-trans-prostadienoic acid.

If one starts with the individual 16α- or 16β-hydroxy isomer, then the corresponding products will also be 16α- or 16β-hydroxy, respectively.

Reference Example 7

Preparation of 9α,11α,16-trihydroxy-16-methyl-19-chloro-20-nor-5-cis,13-trans prostadienoic acid To a stirred solution of 9-oxo-11α,16-dihydroxy-16-methyl-19-chloro-20-nor-5-cis,13-trans-prostadienoic acid in tetrahydrofuran (THF) at −78° C. is added an excess of a 0.5 M solution of lithium perhydro-9b-boraphenalyl hydride in THF. After 30 min. at −78° C., the solution is warmed to 0° C. and treated with water. This mixture is partitioned with ether-potassium-carbonate solutions. The aqueous phase is carefully acidified with hydrochloric acid, saturated with sodium chloride, and extracted with ethyl acetate. The organic extract is washed with brine, dried with magnesium sulfate, and concentrated in vacuo.

The residue is subjected to silica-gel dry column chromatography to provide 9α,11α,16-trihydroxy-16-methyl-19-chloro-20-nor-5-cis,13-trans-prostadienoic acid which may be separated into the individual 16α- and 16β-hydroxyl isomers by HPLC techniques.

Reference Example 8

Preparation of 9-oxo-16-hydroxy-16-methyl-19-chloro-20-nor-10,13,trans-prostadienoic acid 9-oxo-11α,16-dihydroxy-16-methyl-19-chloro-20-nor-13-trans-prostenoic acid is dissolved in a 1:1 tetrahydrofuran-water mixture containing 0.5 N HCl and allowed to stand at ambient temperature under argon for 72 hours. The solution is treated with brine and extracted with ether. The extract is washed with brine, dried over magnesium sulfate, and concentrated in vacuo to an oil. This residue is purified by dry column chromatography to give 9-oxo-16-hydroxy-16-methyl-19-chloro-20-nor-10,13-trans-prostadienoic acid.

If one utilizes the individual 16α or 16β isomer, the product obtained is the 16α- or 16β- epimer respectively.

Reference Example 9

Preparation of 9α,16-dihydroxy-11-oxo-16-methyl-19-chloro-20-nor-13-trans-prostenoic acid To a solution of 9α,11α,16-trihydroxy-16-methyl-19-chloro-20-nor-13-trans-prostenoic acid in acetone (12 ml/g.) at −35° C. is added, dropwise, with stirring, one eqivalent of Jones reagent (2.67 g $CrO_3$ and 2.3 ml of concentrated $H_2SO_4$ diluted to 10 ml with water). After 15 minutes, isopropanol is added, followed by water. The mixture is poured into water. saturated with sodium chloride, extracted with ethyl acetate, dried over magnesium sulfate, and concentrated in vacuo to an oil.

This oil is chromatographed on a dry column of silica-gel using ethyl acetate/heptane mixtures containing 1% acetic acid, to provide the product above.

If one starts with either of the individual 16α- or 16β-hydroxy isomers, one isolates the 16α- or 16β-hydroxy isomer, respectively.

Reference Example 10

Preparation of 7-chloro-hept-1-en-2-one

To a suspension of 28 g (0.21 mol) of aluminum trichloride in 75 ml of $CH_2Cl_2$ at −20° C. is added with stirring a mixture of 20 g (0.2 mol) of vinyltrimethylsilane and 28.2 g (0.2 mol) of 4-chlorobutrylchloride dropwise over 45 min. The mixture is stirred at −20° C. for 4 hr. and kept at 0° for 18 hr. The mixture is poured into 300 g of ice containing 50 g $NH_4Cl$ and stirred until all solids are dissolved. The mixture is extracted with ether and the combined ether extracts are washed with saturated $NaHCO_3$ and dried over magnesium sulfate. The ether is removed in vacuo and the residue distilled (50°–60° C., 0.125 mm) to give a light yellow liquid (14.9 g).

Reference Example 11

Preparation of 7-chloro-4-hydroxy-4-vinyl-1-heptyne

To a suspension of 3.0 g (0.12 mol) of magnesium metal in 10 ml ether containing 100 mg of $HgCl_2$ is added with stirring, under argon, 0.3 ml of $BrCH_2CH_2Br$. After 5 minutes a reaction is initiated and 0.5 g of 80% propargylbromide in toluene is added. Upon evidence of a vigorous reaction, an additional 25 ml of ether is introduced.

A mixture of 13 g (0.1 mol) of 7-chlorohept-1-en-2-one and 19.5 g (0.12 mol) of propargylbromide in 35 ml ether is added at such a rate to maintain a vigorous reflux.

After addition is complete, stirring is continued for 10 minutes. The mixture is cooled to 0° and saturated $NH_4Cl$ is added slowly. The mixture is filtered through diatomaceous earth and the ether is removed in vacuo to provide the title product as an oil.

Reference Example 12

Preparation of 7-chloro-4-trimethylsilyloxy-4-vinyl-1-heptyne

The alcohol from the previous example is disolved in DMF (25 ml) and 16.58 g of imidazole and 13.3 g of chlorotrimethylsilane is added. After stirring at ambient temperature for 1 hour, the reaction mixture is poured into ice water and extracted with petroleum ether. The organic extracts are washed with saturated NaHCO$_3$, dried over magnesium sulfate, and concentrated in vacuo to provide an oil. This residue is distilled (76°–82° C., 0.88 mm) to afford 20.4 g of the title product as a colorless oil.

Reference Example 13

Preparation of E-7-Chloro-4-trimethylsilyloxy-4-vinyl-1-tri-n-butyl-stannyl-1-heptene A mixture of 7-chloro-4-trimethylsilyloxy-4-vinyl-1-heptyne (17 g, 0.07 mol) and 20.7 g (0.71 mol) of tri-n-butylstannane and 150 mg of azobisisobutrylnitrile (AIBN) is stirred under argon in a 140° oil bath behind a safety shield. After 3 minutes an exotherm occurs and the mixture is maintained at 140° C. for 1.5 hr. After cooling, air is admitted and the unreacted tri-n-butylstannane is removed by distillation via Kuglerohr (140°, 0.5–0.3 mm) to give a very light yellow oil (30 g). This oil consists of a mixture of the E and Z isomers.

Reference Example 14

1-trimethylsilyl-3-oxo-6-chloro-1-hexyne

To a stirred solution of 16.8 grams of 4-chlorobutyryl chloride and 20.4 grams of bis-trimethylsilylacetylene in 300 ml of dry methylene chloride, cooled in an ice bath, is added powdered anhydrous aluminum chloride, portionwise, over a period of 20 minutes. The mixture is stirred for 5 minutes, then the cooling bath is removed and the mixture stirred at room temperature for 4 hours. The mixture is poured into 500 ml of ice-water. The organic layer is separated, washed with water and brine, dried over anhydrous sodium sulfate and filtered through diatomaceous earth. The mother liquor is evaporated to dryness giving a brownish residue. The residue is Kugelrohr-distilled to give a colorless liquid.

Reference Example 14a

In the manner described hereinabove in Reference Example 11, 1-trimethylsilyl-3-oxo-6-chloro-1-hexyne is reacted with propargyl magnesium bromide to give 7-chloro-4-hydroxy-4-trimethylsilylethynyl-1-heptyne.

Reference Example 15

7-chloro-4-trimethylsilyloxy-4-trimethylsilylethynyl-1-heptyne

To a stirred mixture of 8.5 grams of 7-chloro-4-hydroxy-4-trimethylsilylethynyl-1-heptyne and 6.2 grams of imidazole in 24 ml of dry dimethylformamide is added, under nitrogen, 5.7 ml of chloro-trimethylsilane, in a slow stream, via a syringe. The mixture is stirred in an ice bath for one hour and then at room temperature overnight. The mixture is poured into hexane, washed with saturated sodium bicarbonate solution, water and then brine and dried over sodium sulfate. The solvents are evaporated to dryness yielding the desired product.

Reference Example 16

E-7-chloro-4-Trimethylsilylethynyl-4-trimethylsiloxy-1-heptene-1-tri-n-butyl stannane To a mixture of 10 mg of azobisisobutyronitrile and 2.94 grams of 7-chloro-4-trimethylsilyloxy-4-trimethylsilylethynyl-1-heptyne is added 2.65 ml of tri-n-butyl stannane via a syringe. The mixture is stirred and heated under nitrogen in an oil bath at 130° C. for about 3 hours and then cooled to room temperature. The mixture is vacuumdistilled through a short-path distillation apparatus to remove a forerun of unreacted tri-n-butyl stannane. The yellow oil (pot residue) comprises the desired product as a mixture of E and Z isomers.

Reference Example 17

15-Deoxy-16-hydroxy-16-trimethylsilylethynyl-19-chloro-20-nor-PGE$_2$

A solution of 5 grams of E/Z-7-chloro-4-trimethylsilylethynyl-4-trimethylsilyloxy-1-hepten-1-tri-n-butyl stannane in 3 ml of tetrahydrofuran is cooled in a dry ice-acetone bath under nitrogen, treated with 6.4 mmol of n-butyl lithium during 10 minutes, stirred at −70° C. for 5 minutes, then at −40° C. for about one hour and finally at −40° C. to −30° C. for 30 minutes.

A second mixture of 830 mg of copper pentyne, 2.55 grams of tri-n-butyl phosphine and 6 ml of ether is stirred at room temperature under nitrogen for about 20 minutes until a clear solution is obtained. The copper pentyne solution is transferred to the vinyl lithium solution (which is first recooled to −75° C. in a dry ice-acetone bath) via a 2.1 grams of cyclopentenone-bis-TMS [U.S. Pat. No. 3,873,607 (Example 1125)] is added during 10 minutes. The mixture is stirred at −78° C. for 10 minutes, then at −50° C. to −40° C. for about one hour, then at −40° C. to −30° C. for 30 minutes and is then recooled to −50° C. The mixture is quenched by pouring it into a mixture of 200 ml of saturated ice-cold ammonium chloride solution and 100 ml of ether. The mixture is extracted with ethyl acetate. The combined ether-ethyl acetate extract is washed with water and brine. The solvents are evaporated to dryness. The residue is treated with 30 ml of acetic acid, 15 ml of tetrahydrofuran and 7.5 ml of water and stirred at room temperature under nitrogen for about 30 minutes. A 50 ml portion of toluene is added and the mixture is evaporated to dryness. The residue is applied to 12 grams of silica gel and then washed with 75 ml of hexane. The silica gel cake is washed with 150 ml of ethyl acetate. The ethyl acetate extract is passed through a dry 2 inch ×50 inch column of 610 grams of silica gel and eluted with 450 ml of 70% ethyl acetate:1% acetic acid in hexane. The product is then eluted from the silica gel with ethyl acetate. The solvent is evaporated to dryness in the presence of toluene giving the desired product.

Reference Example 18

15-Deoxy-16-hydroxy-16-ethynyl-19-chloro-20-nor-PGE$_2$

To a solution of 300 mg of 15-deoxy-16-hydroxy-16-trimethylsilylethynyl-19-chloro-20-nor-PGE$_2$ in 1.2 ml of methanol is added dropwise a solution of 2.7 grams of silver nitrate in 6 ml of water and 18 ml of ethanol. The mixture is then stirred at room temperature under nitrogen for one hour. One ml of a solution of one gram of potassium cyanide in 1–5 ml of water is added and the mixture stirred at room temperature for about 40 minutes. Water is added to dissolve the resulting white precipitate and the solution is neutralized with 5% hydrochloric acid. The white solid which formed is removed. The mother liquor is extracted with ether-ethyl acetate and the organic phase is washed with water and brine, filtered and then evaporated to dryness. The residue is purified through a 200 gram silica gel column (1 3/16 inch×45 inch) and is eluted with 70% ethyl acetate:1% acetic acid in hexane. The product fraction is eluted from the column with ethyl acetate. The solvent is evaporated to dryness in the presence of toluene yielding the desired product as an oily residue.

Reference Example 19

Preparation of
E-7-chloro-4-triethylsilyloxy-1-tri-n-butylstannyl-1-heptene

Treatment of 4-chlorobutyraldehyde by the procedures of Reference Examples 1 to 3 (utilizing chlorotriethylsilane) is productive of the title compound and the intermediates shown in Table A.

TABLE A

| Starting Carbonyl | Hydroxyalkyne | Silyloxyalkyne | Vinylstannane |
|---|---|---|---|
| 4-chlorobutyraldehyde | 7-chloro-4-hydroxy-1-heptyne | 7-chloro-4-triethylsilyloxy-1-heptyne | E-7-chloro-4-triethylsilyloxy-1-tri-n-butylstannyl-1-heptene and the corresponding Z isomer |

Reference Example 20

1,9-Dioxo-11α,16-dihydroxy-1-hydroxymethyl-16-methyl-19-chloro-20-nor-5-cis-13-trans-prostadiene To a solution of 10.8 g. of E/Z-1-tri-n-butylstannyl-7-chloro-4-methyl-4-trimethylsilyloxy-1-heptyne in 11 ml. of tetrahydrofuran at −78° C. under argon, is added with stirring 6.25 ml. of 2.2 M. n-butyllithium. After stirring for 2 hours at −30° to −20° C. a solution of 2.1 g. of pentynyl copper and 5.4 g. of hexamethylphosphoramide in 40 ml. of ether is added at −78° C. After 45 minutes, 2.63 g. of 4-(1-methoxy-1-methylethoxy)-2-[7-oxo-8-(1-methoxy-1-methylethoxy)-2-cis-octenyl]-cyclopent-2-en-1-one is added. The mixture is maintained at −50° to −45° C. for one hour, then at −45° to −20° C. for ½ hour, recooled to −35° C. and 5 ml. of acetic acid followed by saturated ammonium chloride solution are added. The mixture is extracted with ether. The ether solution is washed with dilute hydrochloric acid and the solvent is removed. The residue is stirred in 60 ml. of a solution of acetic acid:tetrahydrofuran:water (4:2:1) at 45° C., under argon for 45 minutes. The solvent is removed at reduced pressure and the residue is dissolved in ethyl acetate and washed with sodium bicarbonate-ammonium chloride solution. The solution is dried over magnesium sulfate and the solvent removed giving a yellow oil. This oil is purified by conventional chromatography, giving the desired product.

Reference Example 21

1,9-Dioxo-11α,16-dihydroxy-1-hydroxymethyl-16-methyl-19-chloro-20-nor-13-trans-prostene To a stirred solution of 1.3 g. of E-7-chloro-1-iodo-4-methyl-4-trimethylsilyloxy-1-heptene in 2 ml. of dry toluene at −78° C. under argon is added 1.5 ml. of 2 M. n-butyllithium, dropwise over 5 minutes. The mixture is stirred at −40° C. for 1.5 hours, recooled to −78° C. and a mixture of 0.4 g. of pentynyl copper and 1.0 g. of hexamethylphosphoramide in 9 ml. of ether is added dropwise over 5 minutes. The mixture is stirred for one hour at −78° C. and 1.5 g. of 4-(1-methoxy-1-methylmethoxy)-2-[8-(1-methoxy-1-methoxymethyl)-7-oxo-octenyl]cyclopent-2-en-1-one in 5 ml. of ether is added. The mixture is stirred at −50° C. for one hour, allowed to warm slowly to −22° to 20° C. over 45 minutes, recooled to −40° C. and 40 ml. of cold saturated ammonium chloride solution and 20 ml. of ether are added. The mixture is stirred ½ hour, extracted twice with ether and the combined ether extracts are washed with two 30 ml. portions of cold dilute hydrochloric acid, 40 ml. of saturated sodium bicarbonate solution and sodium chloride solution, dried over magnesium sulfate, concentrated and stored in a freezer overnight. The resulting oil is stirred with 20 ml. of a mixture of acetic acid:tetrahydrofuran:water (4:2:1) for one hour at 40° C. and then concentrated on a rotary evaporator, adding toluene frequently to remove the acetic acid. The mixture is diluted with ethyl acetate, washed with saturated sodium bicarbonate solution, dried over magnesium sulfate and chromatographed on a silica gel column, eluting with ethyl acetate:heptane (4:1) to give the desired product.

Although in Tables I and II which follow, the product listed is the dl-racemic product, when the cyclopentenone employed is the optically active cyclopentenone (such as (17)) the application of HPLC, column or thin layer chromatography will prove the individual nat. 16α and nat. 16β prostaglandins.

The cyclopentenones of Table B which follows are employed by the addition reaction of Tables I and II.

TABLE B

CYCLOPENTENONES

A. 2-(5-Carbotrimethylsiloxypent-2-cis-enyl-4-trimethylsiloxycyclopent-2-en-1-one
B. 2-(6-Carbotrimethylsiloxyhex-2-cis-enyl)-4-trimethylsiloxycyclopent-2-en-1-one
C. 2-(7-Carbotrimethylsiloxyhept-2-cis-enyl-4-trimethylsiloxycyclopent-2-en-1-one
D. 2-(5-Carbotrimethylsiloxypentyl)-4-trimethylsiloxycyclopent-2-en-1-one
E. 2-(6-Carbotrimethylsiloxyhexyl)-4-trimethylsiloxycyclopent-2-en-1-one
F. 2-(7-Carbotrimethylsiloxyheptyl)-4-trimethylsiloxycyclopent-2-en-1-one
G. 2-(6-Carbotrimethylsiloxy-5-thia-hexyl)-4-trimethylsiloxycyclopent-2-en-1-one
H. 2-(6-Carbotrimethylsiloxy-5-oxa-hexyl)-4-trimethylsiloxycyclopent-2-en-1-one
I. 2-(6-Carbotrimethylsiloxyhex-2-cis-enyl)-4R-trimethylsiloxycyclopent-2-en-1-one
J. 2-6(-Carbotrimethylsiloxyhexyl)-4R-trimethylsiloxycyclopent-2-en-1-one
K. 2-(5-Carboethoxypent-2-cis-enyl)cyclopent-2-en-1-one
L. 2-(6-Carboethoxyhex-2-cis-enyl)cyclopent-2-en-1-one
M. 2-(7-Carboethoxyhept-2-cis-enyl)cyclopent-2-en-1-one
N. 2-(5-Carboethoxypentyl)cyclopent-2-en-1-one
O. 2-(6-Carboethoxyhexyl)cyclopent-2-en-1-one
P. 2-(7-Carboethoxyheptyl)cyclopent-2-en-1-one
Q. 2-(6-Carboethoxy-5-thiahexyl)cyclopent-2-en-1-one
R. 2-(6-Carboethoxy-5-oxahexyl)cyclopent-2-en-1-one Although in Tables I and II which follow, the product listed is the dl-racemic product, when the cyclopentenone employed is the optically active cyclopentenone (such as (17)) the application of HPLC, column or thin layer chromatography will prove the individual nat. 16α and nat. 16β prostaglandins.

TABLE I

Treatment of the appropriate cyclopentenones of Table B with the lithiocuprates derived from the vinylstannanes or vinyliodides of Reference Examples 3, 5, 13, 16 and 19 by the procedures of Reference Examples 4 and 17 is productive of the PGE$^1$ derivatives of Examples 1–44 of Table I. In the case of the 16-ethynyl derivatives, the trimethylsilylethynyl group is cleaved according to Reference Example 18.

| EXAMPLE | VINYL IODIDE | CYCLOPENTENONE | PRODUCT PROSTAGLANDIN OF THE PGE1 SERIES |
|---|---|---|---|
| 1 | 1-trans-iodo-7-chloro 4-triethylsiloxy-1-heptene | 2-(5-carbotrimethylsiloxypentyl)-4-trimethylsiloxycyclopent-2-en-1-one | dl-11α,16-dihydroxy-9-oxo-19-chloro-2-nor-20-nor-13-trans prostenoic acid |
| 2 | 1-trans-iodo-4-methyl-7-chloro 4-trimethylsiloxy-1-heptene | 2-(5-carbotrimethylsiloxypentyl)-4-trimethylsiloxycyclopent-2-en-1-one | dl-11α,16-dihydroxy-9-oxo-16-methyl-19-chloro-2-nor-20-nor-13-trans prostenoic acid |
| 3 | 1-trans-iodo-4-vinyl-7-chloro 4-trimethylsiloxy-1-heptene | 2-(5-carbotrimethylsiloxypentyl)-4-trimethylsiloxycyclopent-2-en-1-one | dl-11α,16-dihydroxy-9-oxo-16-vinyl-19-chloro-2-nor-20-nor-13-trans prostenoic acid |
| 4 | 1-trans-iodo-4-trimethylsilylethynyl-7-chloro 4-trimethylsiloxy-1-heptene | 2-(5-carbotrimethylsiloxypentyl)-4-trimethylsiloxycyclopent-2-en-1-one | dl-11α,16-dihydroxy-9-oxo-16-ethynyl-19-chloro-2-nor-20-nor-13-trans prostenoic acid |
| 5 | 1-trans-iodo-7-chloro 4-trimethylsiloxy-1-heptene | 2-(6-carbotrimethylsiloxyhexyl)-4-trimethylsiloxycyclopent-2-en-1-one | dl-11α,16-dihydroxy-9-oxo-19-chloro-20-nor-13-trans prostenoic acid |
| 6 | 1-trans-iodo-4-methyl-7-chloro 4-triethylsiloxy-1-heptene | 2-(6-carbotrimethylsiloxyhexyl)-4-trimethylsiloxycyclopent-2-en-1-one | dl-11α,16-dihydroxy-9-oxo-16-methyl-19-chloro-20-nor-13-trans prostenoic acid |
| 7 | 1-trans-iodo-4-vinyl-7-chloro 4-trimethylsiloxy-1-heptene | 2-(6-carbotrimethylsiloxyhexyl)-4-trimethylsiloxycyclopent-2-en-1-one | dl-11α,16-dihydroxy-9-oxo-16-vinyl-19-chloro-20-nor-13-trans prostenoic acid |
| 8 | 1-trans-iodo-4-trimethylsilylethynyl-7-chloro 4-trimethylsiloxy-1-heptene | 2-(6-carbotrimethylsiloxyhexyl)-4-trimethylsiloxycyclopent-2-en-1-one | dl-11α,16-dihydroxy-9-oxo-16-ethynyl-19-chloro-20-nor-13-trans prostenoic acid |
| 9 | 1-trans-iodo-7-chloro 4-triethylsiloxy-1-heptene | 2-(7-carbotrimethylsiloxyheptyl)-4-trimethylsiloxycyclopent-2-en-1-one | dl-11α,16-dihydroxy-9-oxo-19-chloro-2-homo-20-nor-13-trans prostenoic acid |
| 10 | 1-trans-iodo-4-methyl-7-chloro 4-trimethylsiloxy-1-heptene | 2-(7-carbotrimethylsiloxyheptyl)-4-trimethylsiloxycyclopent-2-en-1-one | dl-11α,16-dihydroxy-9-oxo-16-methyl-19-chloro-2-homo-20-nor-13-trans prostenoic acid |
| 11 | 1-trans-iodo-4-vinyl-7-chloro 4-trimethylsiloxy-1-heptene | 2-(7-carbotrimethylsiloxyheptyl)-4-trimethylsiloxycyclopent-2-en-1-one | dl-11α,16-dihydroxy-9-oxo-16-vinyl-19-chloro-2-homo-20-nor-13-trans prostenoic acid |
| 12 | 1-trans-iodo-4-trimethylsilylethynyl-7-chloro 4-trimethylsiloxy-1-heptene | 2-(7-carbotrimethylsiloxyheptyl)-4-trimethylsiloxycyclopent-2-en-1-one | dl-11α,16-dihydroxy-9-oxo-16-ethynyl-19-chloro-2-homo-20-nor-13-trans prostenoic acid |
| 13 | 1-trans-iodo-7-chloro 4-triethylsiloxy-1-heptene | 2-(6-carbotrimethylsiloxy-5-thiahexyl)-4-trimethylsiloxycyclopent-2-en-1-one | dl-11α,16-dihydroxy-9-oxo-19-chloro-20-nor-3-thia-13-trans prostenoic acid |
| 14 | 1-trans-iodo-4-methyl-7-chloro 4-trimethylsiloxy-1-heptene | 2-(6-carbotrimethylsiloxy-5-thiahexyl)-4-trimethylsiloxycyclopent-2-en-1-one | dl-11α,16-dihydroxy-9-oxo-16-methyl-19-chloro-20-nor-3-thia-13-trans prostenoic acid |
| 15 | 1-trans-iodo-4-vinyl-7-chloro 4-trimethylsiloxy-1-heptene | 2-(6-carbotrimethylsiloxy-5-thiahexyl)-4-trimethylsiloxycyclopent-2-en-1-one | dl-11α,16-dihydroxy-9-oxo-16-vinyl-19-chloro-20-nor-3-thia-13-trans prostenoic acid |
| 16 | 1-trans-iodo-4-trimethylsilylethynyl-7-chloro 4-trimethylsiloxy-1-heptene | 2-(6-carbotrimethylsiloxy-5-thiahexyl)-4-trimethylsiloxycyclopent-2-en-1-one | dl-11α,16-dihydroxy-9-oxo-16-ethynyl-19-chloro-20-nor-3-thia-13-trans prostenoic acid |
| 17 | 1-trans-iodo-7-chloro 4-triethylsiloxy-1-heptene | 2-(6-carbotrimethylsiloxy-5-oxahexyl)-4-trimethylsiloxycyclopent-2-en-1-one | dl-11α,16-dihydroxy-9-oxo-19-chloro-20-nor-3-oxa-13-trans prostenoic acid |
| 18 | 1-trans-iodo-4-methyl-7-chloro 4-trimethylsiloxy-1-heptene | 2-(6-carbotrimethylsiloxy-5-oxahexyl)-4-trimethylsiloxycyclopent-2-en-1-one | dl-11α,16-dihydroxy-9-oxo-16-methyl-19-chloro-20-nor-3-oxa-13-trans prostenoic acid |
| 19 | 1-trans-iodo-4-vinyl-7-chloro 4-trimethylsiloxy-1-heptene | 2-(6-carbotrimethylsiloxy-5-oxahexyl)-4-trimethylsiloxycyclopent-2-en-1-one | dl-11α,16-dihydroxy-9-oxo-16-vinyl-19-chloro-20-nor-3-oxa-13-trans prostenoic acid |
| 20 | 1-trans-iodo-4-trimethylsilylethynyl-7-chloro 4-trimethylsiloxy-1-heptene | 2-(6-carbotrimethylsiloxy-5-oxahexyl)-4-trimethylsiloxycyclopent-2-en-1-one | dl-11α,16-dihydroxy-2-oxo-16-ethynyl-19-chloro-20-nor-3-oxa-13-trans prostenoic acid |
| 21 | 1-trans-iodo-7-chloro 4-triethylsiloxy-1-heptene | 2-(6-carbotrimethylsiloxyhexyl)-4R-trimethylsiloxycyclopent-2-en-1-one | nat-11α,16-dihydroxy-9-oxo-19-chloro-20-nor-13-trans prostenoic acid |
| 22 | 1-trans-iodo-4-methyl-7-chloro 4-trimethylsiloxy-1-heptene | 2-(6-carbotrimethylsiloxyhexyl)-4R-trimethylsiloxycyclopent-2-en-1-one | nat-11α,16-dihydroxy-9-oxo-16-methyl-19-chloro-20-nor-13-trans prostenoic acid |
| 23 | 1-trans-iodo-4-vinyl-7-chloro 4-trimethylsiloxy-1-heptene | 2-(6-carbotrimethylsiloxyhexyl)-4R-trimethylsiloxycyclopent-2-en-1-one | nat-11α,16-dihydroxy-9-oxo-16-vinyl-19-chloro-20-nor-13-trans prostenoic acid |
| 24 | 1-trans-iodo-4-trimethylsilylethynyl-7-chloro 4-trimethylsiloxy-1-heptene | 2-(6-carbotrimethylsiloxyhexyl)-4R-trimethylsiloxycyclopent-2-en-1-one | nat-11α,16-dihydroxy-9-oxo-16-ethynyl-19-chloro-20-nor-13-trans prostenoic acid |

| EXAMPLE | VINYL IODIDE | CYCLOPENTENONE | PRODUCT PROSTAGLANDIN OF THE 11-DEOXY PGE1 SERIES |
|---|---|---|---|
| 25 | 1-trans-iodo-7-chloro | 2-(5-carboethoxypentyl) | dl-16-hydroxy-9-oxo-19-chloro- |

-continued

| # | | |
|---|---|---|
| 26 | 4-triethylsiloxy-1-heptene | cyclopent-2-en-1-one | 2-nor-20-nor-13-trans prostenoic acid |
| 27 | 1-trans-iodo-4-methyl-7-chloro | 2-(5-carboethoxypentyl)cyclopent-2-en-1-one | dl-16-hydroxy-9-oxo-16-methyl-19-chloro-2-nor-20-nor-13-trans prostenoic acid |
| 28 | 4-trimethylsiloxy-1-heptene | 2-(5-carboethoxypentyl)cyclopent-2-en-1-one | dl-16-hydroxy-9-oxo-16-vinyl-19-chloro-2-nor-20-nor-13-trans prostenoic acid |
| | 1-trans-iodo-4-trimethylsilylethynyl-7-chloro | 2-(5-carboethoxypentyl)cyclopent-2-en-1-one | dl-16-hydroxy-9-oxo-16-ethynyl-19-chloro-2-nor-20-nor-13-trans prostenoic acid |
| 29 | 4-trimethylsiloxy-1-heptene | 2-(6-carboethoxyhexyl)cyclopent-2-en-1-one | dl-16-hydroxy-9-oxo-19-chloro-20-nor-13-trans prostenoic acid |
| 30 | 1-trans-iodo-4-methyl-7-chloro | 2-(6-carboethoxyhexyl)cyclopent-2-en-1-one | dl-16-hydroxy-9-oxo-16-methyl-19-chloro-20-nor-13-trans prostenoic acid |
| 31 | 4-trimethylsiloxy-1-heptene | 2-(6-carboethoxyhexyl)cyclopent-2-en-1-one | dl-16-hydroxy-9-oxo-16-vinyl-19-chloro-20-nor-13-trans prostenoic acid |
| 32 | 1-trans-iodo-4-trimethylsilylethynyl-7-chloro | 2-(6-carboethoxyhexyl)cyclopent-2-en-1-one | dl-16-hydroxy-9-oxo-16-ethynyl-19-chloro-20-nor-13-trans prostenoic acid |
| 33 | 4-triethylsiloxy-1-heptene | 2-(7-carboethoxyheptyl)cyclopent-2-en-1-one | dl-16-hydroxy-9-oxo-19-chloro-2-homo-20-nor-13-trans prostenoic acid |
| 34 | 1-trans-iodo-4-methyl-7-chloro | 2-(7-carboethoxyheptyl)cyclopent-2-en-1-one | dl-16-hydroxy-9-oxo-16-methyl-19-chloro-2-homo-20-nor-13-trans prostenoic acid |
| 35 | 4-trimethylsiloxy-1-heptene | 2-(7-carboethoxyheptyl)cyclopent-2-en-1-one | dl-16-hydroxy-9-oxo-16-vinyl-19-chloro-2-homo-20-nor-13-trans prostenoic acid |
| 36 | 1-trans-iodo-4-trimethylsilylethynyl-7-chloro | 2-(7-carboethoxyheptyl)cyclopent-2-en-1-one | dl-16-hydroxy-9-oxo-16-ethynyl-19-chloro-2-homo-20-nor-13-trans prostenoic acid |
| 37 | 4-trimethylsiloxy-1-heptene | 2-(6-carboethoxy-5-thiahexyl)cyclopent-2-en-1-one | dl-16-hydroxy-9-oxo-19-chloro-20-nor-3-thia-13-trans prostenoic acid |
| 38 | 1-trans-iodo-4-methyl-7-chloro | 2-(6-carboethoxy-5-thiahexyl)cyclopent-2-en-1-one | dl-16-hydroxy-9-oxo-16-methyl-19-chloro-20-nor-3-thia-13-trans prostenoic acid |
| 39 | 4-trimethylsiloxy-1-heptene | 2-(6-carboethoxy-5-thiahexyl)cyclopent-2-en-1-one | dl-16-hydroxy-9-oxo-16-vinyl-19-chloro-20-nor-3-thia-13-trans prostenoic acid |
| 40 | 1-trans-iodo-4-trimethylsilylethynyl-7-chloro | 2-(6-carboethoxy-5-thiahexyl)cyclopent-2-en-1-one | dl-16-hydroxy-9-oxo-16-ethynyl-19-chloro-20-nor-3-thia-13-trans prostenoic acid |
| 41 | 4-trimethylsiloxy-1-heptene | 2-(6-carboethoxy-5-oxahexyl)cyclopent-2-en-1-one | dl-16-hydroxy-9-oxo-19-chloro-20-nor-3-oxa-13-trans prostenoic acid |
| 42 | 1-trans-iodo-4-methyl-7-chloro | 2-(6-carboethoxy-5-oxahexyl)cyclopent-2-en-1-one | dl-16-hydroxy-9-oxo-16-methyl-19-chloro-20-nor-3-oxa-13-trans prostenoic acid |
| 43 | 4-trimethylsiloxy-1-heptene | 2-(6-carboethoxy-5-oxahexyl)cyclopent-2-en-1-one | dl-16-hydroxy-9-oxo-16-vinyl-19-chloro-20-nor-3-oxa-13-trans prostenoic acid |
| 44 | 1-trans-iodo-4-trimethylsilylethynyl-7-chloro | 2-(6-carboethoxy-5-oxahexyl)cyclopent-2-en-1-one | dl-16-hydroxy-9-oxo-16-ethynyl-19-chloro-20-nor-3-oxa-13-trans prostenoic acid |

Treatment of the PGE$_1$ derivatives of Examples 1–44 of Table I with lithium perhydro-9b-boraphenalyl hydride by the procedure of Reference Example 6 is productive of the PGF$_1$ and derivatives of Examples 45–88 of Table I.

| EXAMPLE | STARTING PROSTAGLANDIN OF THE PGE SERIES | PRODUCT PROSTAGLANDIN OF THE PGF1α SERIES |
|---|---|---|
| 45 | dl-11α,16-dihydroxy-9-oxo-19-chloro-2-nor-20-nor-13-trans prostenoic acid | dl-9α,11α,16-trihydroxy-19-chloro-2-nor-20-nor-13-trans prostenoic acid |
| 46 | dl-11α,16-dihydroxy-9-oxo-16-methyl-19-chloro-2-nor-20-nor-13-trans prostenoic acid | dl-9α,11α,16-trihydroxy-16-methyl-19-chloro-2-nor-20-nor-13-trans prostenoic acid |
| 47 | dl-11α,16-dihydroxy-9-oxo-16-vinyl-19-chloro-2-nor-20-nor-13-trans prostenoic acid | dl-9α,11α,16-trihydroxy-16-vinyl-19-chloro-2-nor-20-nor-13-trans prostenoic acid |
| 48 | dl-11α,16-dihydroxy-9-oxo-16-ethynyl-19-chloro-2-nor-20-nor-13-trans prostenoic acid | dl-9α,11α,16-trihydroxy-16-ethynyl-19-chloro-2-nor-20-nor-13-trans prostenoic acid |
| 49 | dl-11α,16-dihydroxy-9-oxo-19-chloro-20-nor-13-trans prostenoic acid | dl-9α,11α,16-trihydroxy-19-chloro-20-nor-13-trans prostenoic acid |
| 50 | dl-11α,16-dihydroxy-9-oxo-16-methyl-19-chloro-20-nor-13-trans prostenoic acid | dl-9α,11α,16-trihydroxy-16-methyl-19-chloro-20-nor-13-trans prostenoic acid |
| 51 | dl-11α,16-dihydroxy-9-oxo-16-vinyl-19-chloro-20-nor-13-trans prostenoic acid | dl-9α,11α,16-trihydroxy-16-vinyl-19-chloro-20-nor-13-trans prostenoic acid |
| 52 | dl-11α,16-dihydroxy-9-oxo-16-ethynyl-19-chloro-20-nor-13-trans prostenoic acid | dl-9α,11α,16-trihydroxy-16-ethynyl-19-chloro-20-nor-13-trans prostenoic acid |
| 53 | dl-11α,16-dihydroxy-9-oxo-19-chloro-2-homo-20-nor-13-trans prostenoic acid | dl-9α,11α,16-trihydroxy-19-chloro-2-homo-20-nor-13-trans prostenoic acid |
| 54 | dl-11α,16-dihydroxy-9-oxo-16-methyl-19-chloro-2-homo-20-nor-13-trans prostenoic acid | dl-9α,11α,16-trihydroxy-16-methyl-19-chloro-2-homo-20-nor-13-trans prostenoic acid |
| 55 | dl-11α,16-dihydroxy-9-oxo-16-vinyl-19-chloro-2-homo-20-nor-13-trans prostenoic acid | dl-9α,11α,16-trihydroxy-16-vinyl-19-chloro-2-homo-20-nor-13-trans prostenoic acid |
| 56 | dl-11α,16-dihydroxy-9-oxo-16-ethynyl-19-chloro-2-homo-20-nor-13-trans prostenoic acid | dl-9α,11α,16-trihydroxy-16-ethynyl-19-chloro-2-homo-20-nor-13-trans prostenoic acid |
| 57 | dl-11α,16-dihydroxy-9-oxo-19-chloro-20-nor-3-thia-13-trans prostenoic acid | dl-9α,11α,16-trihydroxy-19-chloro-20-nor-3-thia-13-trans prostenoic acid |
| 58 | dl-11α,16-dihydroxy-9-oxo-16-methyl-19-chloro-20-nor-3-thia-13-trans prostenoic acid | dl-9α,11α,16-trihydroxy-16-methyl-19-chloro-20-nor-3-thia-13-trans prostenoic acid |
| 59 | dl-11α,16-dihydroxy-9-oxo-16-vinyl-19-chloro-20-nor-3-thia-13-trans prostenoic acid | dl-9α,11α,16-trihydroxy-16-vinyl-19-chloro-20-nor-3-thia-13-trans prostenoic acid |
| 60 | dl-11α,16-dihydroxy-9-oxo-16-ethynyl-19-chloro-20-nor-3-thia-13-trans prostenoic acid | dl-9α,11α,16-trihydroxy-16-ethynyl-19-chloro-20-nor-3-thia-13-trans prostenoic acid |
| 61 | dl-11α,16-dihydroxy-9-oxo-19-chloro-20-nor-3-oxa-13-trans prostenoic acid | dl-9α,11α,16-trihydroxy-19-chloro-20-nor-3-oxa-13-trans prostenoic acid |
| 62 | dl-11α,16-dihydroxy-9-oxo-16-methyl-19-chloro-20-nor-3-oxa-13-trans prostenoic acid | dl-9α,11α,16-trihydroxy-16-methyl-19-chloro-20-nor-3-oxa-13-trans prostenoic acid |
| 63 | dl-11α,16-dihydroxy-9-oxo-16-vinyl-19-chloro-20-nor-3-oxa-13-trans prostenoic acid | dl-9α,11α,16-trihydroxy-16-vinyl-19-chloro-20-nor-3-oxa-13-trans prostenoic acid |
| 64 | dl-11α,16-dihydroxy-9-oxo-16-ethynyl-19-chloro-20-nor-3-oxa-13-trans prostenoic acid | dl-9α,11α,16-trihydroxy-16-ethynyl-19-chloro-20-nor-3-oxa-13-trans prostenoic acid |
| 65 | nat-11α,16-dihydroxy-9-oxo-19-chloro-20-nor-13-trans prostenoic acid | nat-9α,11α,16-trihydroxy-19-chloro-20-nor-13-trans prostenoic acid |
| 66 | nat-11α,16-dihydroxy-9-oxo-16-methyl-19-chloro-20-nor-13-trans prostenoic acid | nat-9α,11α,16-trihydroxy-16-methyl-19-chloro-20-nor-13-trans prostenoic acid |
| 67 | nat-11α,16-dihydroxy-9-oxo-16-vinyl-19-chloro-20-nor-13-trans prostenoic acid | nat-9α,11α,16-trihydroxy-16-vinyl-19-chloro-20-nor-13-trans prostenoic acid |
| 68 | nat-11α,16-dihydroxy-9-oxo-16-ethynyl-19-chloro-20-nor-13-trans prostenoic acid | nat-9α,11α,16-trihydroxy-16-ethynyl-19-chloro-20-nor-13-trans prostenoic acid |

| EXAMPLE | STARTING PROSTAGLANDIN OF THE PGE SERIES | PRODUCT PROSTAGLANDIN OF THE 11-DEOXY PGF1α SERIES |
|---|---|---|
| 69 | dl-16-hydroxy-9-oxo-19-chloro-2-nor-20-nor-13-trans prostenoic acid | dl-9α,16-dihydroxy-19-chloro-2-nor-20-nor-13-trans prostenoic acid |

-continued

| | | |
|---|---|---|
| 70 | dl-16-hydroxy-9-oxo-16-methyl-19-chloro-2-nor-20-nor-13-trans prostenoic acid | dl-9α,16-dihydroxy-16-methyl-19-chloro-2-nor-20-nor-13-trans prostenoic acid |
| 71 | dl-16-hydroxy-9-oxo-16-vinyl-19-chloro-2-nor-20-nor-13-trans prostenoic acid | dl-9α,16-dihydroxy-16-vinyl-19-chloro-2-nor-20-nor-13-trans prostenoic acid |
| 72 | dl-16-hydroxy-9-oxo-16-ethynyl-19-chloro-2-nor-20-nor-13-trans prostenoic acid | dl-9α,16-dihydroxy-16-ethynyl-19-chloro-2-nor-20-nor-13-trans prostenoic acid |
| 73 | dl-16-hydroxy-9-oxo-19-chloro-20-nor-13-trans prostenoic acid | dl-9α,16-dihydroxy-19-chloro-20-nor-13-trans prostenoic acid |
| 74 | dl-16-hydroxy-9-oxo-16-methyl-19-chloro-20-nor-13-trans prostenoic acid | dl-9α,16-dihydroxy-16-methyl-19-chloro-20-nor-13-trans prostenoic acid |
| 75 | dl-16-hydroxy-9-oxo-16-vinyl-19-chloro-20-nor-13-trans prostenoic acid | dl-9α,16-dihydroxy-16-vinyl-19-chloro-20-nor-13-trans prostenoic acid |
| 76 | dl-16-hydroxy-9-oxo-16-ethynyl-19-chloro-20-nor-13-trans prostenoic acid | dl-9α,16-dihydroxy-16-ethynyl-19-chloro-20-nor-13-trans prostenoic acid |
| 77 | dl-16-hydroxy-9-oxo-19-chloro-2-homo-20-nor-13-trans prostenoic acid | dl-9α,16-dihydroxy-19-chloro-2-homo-20-nor-13-trans prostenoic acid |
| 78 | dl-16-hydroxy-9-oxo-16-methyl-19-chloro-2-homo-20-nor-13-trans prostenoic acid | dl-9α,16-dihydroxy-16-methyl-19-chloro-2-homo-20-nor-13-trans prostenoic acid |
| 79 | dl-16-hydroxy-9-oxo-16-vinyl-19-chloro-2-homo-20-nor-13-trans prostenoic acid | dl-9α,16-dihydroxy-16-vinyl-19-chloro-2-homo-20-nor-13-trans prostenoic acid |
| 80 | dl-16-hydroxy-9-oxo-16-ethynyl-19-chloro-2-homo-20-nor-13-trans prostenoic acid | dl-9α,16-dihydroxy-16-ethynyl-19-chloro-2-homo-20-nor-13-trans prostenoic acid |
| 81 | dl-16-hydroxy-9-oxo-19-chloro-20-nor-3-thia-13-trans prostenoic acid | dl-9α,16-dihydroxy-19-chloro-20-nor-3-thia-13-trans prostenoic acid |
| 82 | dl-16-hydroxy-9-oxo-16-methyl-19-chloro-20-nor-3-thia-13-trans prostenoic acid | dl-9α,16-dihydroxy-16-methyl-19-chloro-20-nor-3-thia-13-trans prostenoic acid |
| 83 | dl-16-hydroxy-9-oxo-16-vinyl-19-chloro-20-nor-3-thia-13-trans prostenoic acid | dl-9α,16-dihydroxy-16-vinyl-19-chloro-20-nor-3-thia-13-trans prostenoic acid |
| 84 | dl-16-hydroxy-9-oxo-16-ethynyl-19-chloro-20-nor-3-thia-13-trans prostenoic acid | dl-9α,16-dihydroxy-16-ethynyl-19-chloro-20-nor-3-thia-13-trans prostenoic acid |
| 85 | dl-16-hydroxy-9-oxo-19-chloro-20-nor-3-oxa-13-trans prostenoic acid | dl-9α,16-dihydroxy-19-chloro-20-nor-3-oxa-13-trans prostenoic acid |
| 86 | dl-16-hydroxy-9-oxo-16-methyl-19-chloro-20-nor-3-oxa-13-trans prostenoic acid | dl-9α,16-dihydroxy-16-methyl-19-chloro-20-nor-3-oxa-13-trans prostenoic acid |
| 87 | dl-16-hydroxy-9-oxo-16-vinyl-19-chloro-20-nor-3-oxa-13-trans prostenoic acid | dl-9α,16-dihydroxy-16-vinyl-19-chloro-20-nor-3-oxa-13-trans prostenoic acid |
| 88 | dl-16-hydroxy-9-oxo-16-ethynyl-19-chloro-20-nor-3-oxa-13-trans prostenoic acid | dl-9α,16-dihydroxy-16-ethynyl-19-chloro-20-nor-3-oxa-13-trans prostenoic acid |

Treatment of the PGE$_1$ derivatives of Examples 1–44 of Table I with sodium borohydride by the procedure of Reference Example 7 is productive of the PGFα and PGFβ derivatives of Examples 89 to 132 of Table I.

| EXAMPLE | STARTING PROSTAGLANDIN OF THE PGE SERIES | PRODUCT PROSTAGLANDIN OF THE PGF1β SERIES |
|---|---|---|
| 89 | dl-11α,16-dihydroxy-9-oxo-19-chloro-2-nor-20-nor-13-trans prostenoic acid | dl-9β,11α,16-trihydroxy-19-chloro-2-nor-20-nor-13-trans prostenoic acid |
| 90 | dl-11α,16-dihydroxy-9-oxo-16-methyl-19-chloro-2-nor-20-nor-13-trans prostenoic acid | dl-9β,11α,16-trihydroxy-16-methyl-19-chloro-2-nor-20-nor-13-trans prostenoic acid |
| 91 | dl-11α,16-dihydroxy-9-oxo-16-vinyl-19-chloro-2-nor-20-nor-13-trans prostenoic acid | dl-9β,11α,16-trihydroxy-16-vinyl-19-chloro-2-nor-20-nor-13-trans prostenoic acid |
| 92 | dl-11α,16-dihydroxy-9-oxo-16-ethynyl-19-chloro-2-nor-20-nor-13-trans prostenoic acid | dl-9β,11α,16-trihydroxy-16-ethynyl-19-chloro-2-nor-20-nor-13-trans prostenoic acid |
| 93 | dl-11α,16-dihydroxy-9-oxo-19-chloro-20-nor-13-trans prostenoic acid | dl-9β,11α,16-trihydroxy-19-chloro-20-nor-13-trans prostenoic acid |
| 94 | dl-11α,16-dihydroxy-9-oxo-16-methyl-19-chloro-20-nor-13-trans prostenoic acid | dl-9β,11α,16-trihydroxy-16-methyl-19-chloro-20-nor-13-trans prostenoic acid |
| 95 | dl-11α,16-dihydroxy-9-oxo-16-vinyl-19-chloro-20-nor-13-trans prostenoic acid | dl-9β,11α,16-trihydroxy-16-vinyl-19-chloro-20-nor-13-trans prostenoic acid |
| 96 | dl-11α,16-dihydroxy-9-oxo-16-ethynyl-19-chloro-20-nor-13-trans prostenoic acid | dl-9β,11α,16-trihydroxy-16-ethynyl-19-chloro-20-nor-13-trans prostenoic acid |
| 97 | dl-11α,16-dihydroxy-9-oxo-19-chloro-2-homo-20-nor-13-trans prostenoic acid | dl-9β,11α,16-trihydroxy-19-chloro-2-homo-20-nor-13-trans prostenoic acid |
| 98 | dl-11α,16-dihydroxy-9-oxo-16-methyl-19-chloro-2-homo-20-nor-13-trans prostenoic acid | dl-9β,11α,16-trihydroxy-16-methyl-19-chloro-2-homo-20-nor-13-trans prostenoic acid |
| 99 | dl-11α,16-dihydroxy-9-oxo-16-vinyl-19-chloro-2-homo-20-nor-13-trans prostenoic acid | dl-9β,11α,16-trihydroxy-16-vinyl-19-chloro-2-homo-20-nor-13-trans prostenoic acid |
| 100 | dl-11α,16-dihydroxy-9-oxo-16-ethynyl-19-chloro-2-homo-20-nor-13-trans prostenoic acid | dl-9β,11α,16-trihydroxy-16-ethynyl-19-chloro-2-homo-20-nor-13-trans prostenoic acid |
| 101 | dl-11α,16-dihydroxy-9-oxo-19-chloro-20-nor-3-thia-13-trans prostenoic acid | dl-9β,11α,16-trihydroxy-19-chloro-20-nor-3-thia-13-trans prostenoic acid |
| 102 | dl-11α,16-dihydroxy-9-oxo-16-methyl-19-chloro-20-nor-3-thia-13-trans prostenoic acid | dl-9β,11α,16-trihydroxy-16-methyl-19-chloro-20-nor-3-thia-13-trans prostenoic acid |
| 103 | dl-11α,16-dihydroxy-9-oxo-16-vinyl-19-chloro-20-nor-3-thia-13-trans prostenoic acid | dl-9β,11α,16-trihydroxy-16-vinyl-19-chloro-20-nor-3-thia-13-trans prostenoic acid |
| 104 | dl-11α,16-dihydroxy-9-oxo-16-ethynyl-19-chloro-20-nor-3-thia-13-trans prostenoic acid | dl-9β,11α,16-trihydroxy-16-ethynyl-19-chloro-20-nor-3-thia-13-trans prostenoic acid |
| 105 | dl-11α,16-dihydroxy-9-oxo-19-chloro-20-nor-13-trans prostenoic acid | dl-9β,11α,16-trihydroxy-9-chloro-20-nor-13-trans prostenoic acid |
| 106 | dl-11α,16-dihydroxy-9-oxo-16-methyl-19-chloro-20-nor-3-oxa-13-trans prostenoic acid | dl-9β,11α,16-trihydroxy-16-methyl-19-chloro-20-nor-3-oxa-13-trans prostenoic acid |
| 107 | dl-11α,16-dihydroxy-9-oxo-16-vinyl-19-chloro-20-nor-3-oxa-13-trans prostenoic acid | dl-9β,11α,16-trihydroxy-16-vinyl-19-chloro-20-nor-3-oxa-13-trans prostenoic acid |
| 108 | dl-11α,16-dihydroxy-9-oxo-16-ethynyl-19-chloro-20-nor-3-oxa-13-trans prostenoic acid | dl-9β,11α,16-trihydroxy-16-ethynyl-19-chloro-20-nor-3-oxa-13-trans prostenoic acid |
| 109 | nat-11α,16-dihydroxy-9-oxo-19-chloro-20-nor-13-trans prostenoic acid | nat-9β,11α,16-trihydroxy-19-chloro-20-nor-13-trans prostenoic acid |
| 110 | nat-11α,16-dihydroxy-9-oxo-16-methyl-19-chloro-20-nor-13-trans prostenoic acid | nat-9β,11α,16-trihydroxy-16-methyl-19-chloro-20-nor-13-trans prostenoic acid |
| 111 | nat-11α,16-dihydroxy-9-oxo-16-vinyl-19-chloro-20-nor-13-trans prostenoic acid | nat-9β,11α,16-trihydroxy-16-vinyl-19-chloro-20-nor-13-trans prostenoic acid |
| 112 | nat-11α,16-dihydroxy-9-oxo-16-ethynyl-19-chloro-20-nor-13-trans prostenoic acid | nat-9β,11α,16-trihydroxy-16-ethynyl-19-chloro-20-nor-13-trans prostenoic acid |

| EXAMPLE | STARTING PROSTAGLANDIN OF THE PGE SERIES | PRODUCT PROSTAGLANDIN OF THE 11-DEOXY PGF1β SERIES |
|---|---|---|
| 113 | dl-16-hydroxy-9-oxo-19-chloro-2-nor-20-nor-13-trans prostenoic acid | dl-9β,16-dihydroxy-19-chloro-2-nor-20-nor-13-trans prostenoic acid |

-continued

| | | |
|---|---|---|
| 114 | dl-16-hydroxy-9-oxo-16-methyl-19-chloro-2-nor-20-nor-13-trans prostenoic acid | dl-9β,16-dihydroxy-16-methyl-19-chloro-2-nor-20-nor-13-trans prostenoic acid |
| 115 | dl-16-hydroxy-9-oxo-16-vinyl-19-chloro-2-nor-20-nor-13-trans prostenoic acid | dl-9β,16-dihydroxy-16-vinyl-19-chloro-2-nor-20-nor-13-trans prostenoic acid |
| 116 | dl-16-hydroxy-9-oxo-16-ethynyl-19-chloro-2-nor-20-nor-13-trans prostenoic acid | dl-9β,16-dihydroxy-16-ethynyl-19-chloro-2-nor-20-nor-13-trans prostenoic acid |
| 117 | dl-16-hydroxy-9-oxo-19-chloro-20-nor-13-trans prostenoic acid | dl-9β,16-dihydroxy-19-chloro-20-nor-13-trans prostenoic acid |
| 118 | dl-16-hydroxy-9-oxo-16-methyl-19-chloro-20-nor-13-trans prostenoic acid | dl-9β,16-dihydroxy-16-methyl-19-chloro-20-nor-13-trans prostenoic acid |
| 119 | dl-16-hydroxy-9-oxo-16-vinyl-19-chloro-20-nor-13-trans prostenoic acid | dl-9β,16-dihydroxy-16-vinyl-19-chloro-20-nor-13-trans prostenoic acid |
| 120 | dl-16-hydroxy-9-oxo-16-ethynyl-19-chloro-20-nor-13-trans prostenoic acid | dl-9β,16-dihydroxy-16-ethynyl-19-chloro-20-nor-13-trans prostenoic acid |
| 121 | dl-16-hydroxy-9-oxo-19-chloro-2-homo-20-nor-13-trans prostenoic acid | dl-9β,16-dihydroxy-19-chloro-2-homo-20-nor-13-trans prostenoic acid |
| 122 | dl-16-hydroxy-9-oxo-16-methyl-19-chloro-2-homo-20-nor-13-trans prostenoic acid | dl-9β,16-dihydroxy-16-methyl-19-chloro-2-homo-20-nor-13-trans prostenoic acid |
| 123 | dl-16-hydroxy-9-oxo-16-vinyl-19-chloro-2-homo-20-nor-13-trans prostenoic acid | dl-9β,16-dihydroxy-16-vinyl-19-chloro-2-homo-20-nor-13-trans prostenoic acid |
| 124 | dl-16-hydroxy-9-oxo-16-ethynyl-19-chloro-2-homo-20-nor-13-trans prostenoic acid | dl-9β,16-dihydroxy-16-ethynyl-19-chloro-2-homo-20-nor-13-trans prostenoic acid |
| 125 | dl-16-hydroxy-9-oxo-19-chloro-20-nor-3-thia-13-trans prostenoic acid | dl-9β,16-dihydroxy-19-chloro-20-nor-3-thia-13-trans prostenoic acid |
| 126 | dl-16-hydroxy-9-oxo-16-methyl-19-chloro-20-nor-3-thia-13-trans prostenoic acid | dl-9β,16-dihydroxy-16-methyl-19-chloro-20-nor-3-thia-13-trans prostenoic acid |
| 127 | dl-16-hydroxy-9-oxo-16-vinyl-19-chloro-20-nor-3-thia-13-trans prostenoic acid | dl-9β,16-dihydroxy-16-vinyl-19-chloro-20-nor-3-thia-13-trans prostenoic acid |
| 128 | dl-16-hydroxy-9-oxo-16-ethynyl-19-chloro-20-nor-3-thia-13-trans prostenoic acid | dl-9β,16-dihydroxy-16-ethynyl-19-chloro-20-nor-3-thia-13-trans prostenoic acid |
| 129 | dl-16-hydroxy-9-oxo-19-chloro-20-nor-3-oxa-13-trans prostenoic acid | dl-9β,16-dihydroxy-19-chloro-20-nor-3-oxa-13-trans prostenoic acid |
| 130 | dl-16-hydroxy-9-oxo-16-methyl-19-chloro-20-nor-3-oxa-13-trans prostenoic acid | dl-9β,16-dihydroxy-16-methyl-19-chloro-20-nor-3-oxa-13-trans prostenoic acid |
| 131 | dl-16-hydroxy-9-oxo-16-vinyl-19-chloro-20-nor-3-oxa-13-trans prostenoic acid | dl-9β,16-dihydroxy-16-vinyl-19-chloro-20-nor-3-oxa-13-trans prostenoic acid |
| 132 | dl-16-hydroxy-9-oxo-16-ethynyl-19-chloro-20-nor-3-oxa-13-trans prostenoic acid | dl-9β,16-dihydroxy-16-ethynyl-19-chloro-20-nor-3-oxa-13-trans prostenoic acid |

TABLE II

Treatment of the appropriate cyclopentenones of Table B with the lithiocuprates derived from the vinylstannanes or vinyliodides of Reference Examples 3, 5, 13, 16 and 19 by the procedures of Reference Examples 4 and 17 is productive of the PGE$^1$ derivatives of Examples 1–28 of Table II. In the case of the 16-ethynyl derivatives the trimethylsilylethynyl group is cleaved according to Reference Example 18.

| EXAMPLE | VINYL IODIDE | CYCLOPENTENONE | PRODUCT PROSTAGLANDIN OF THE PGE2 SERIES |
|---|---|---|---|
| 1 | 1-trans-iodo-7-chloro-1-heptene | 2-(5-carbotrimethylsiloxypent-2-cis-enyl)-4-trimethylsiloxycyclopent-2-en-1-one | dl-11α,16-dihydroxy-9-oxo-19-chloro-2-nor-20-nor-5-cis-13-trans prostadienoic acid |
| 2 | 4-triethylsiloxy-1-heptene | 2-(5-carbotrimethylsiloxypent-2-cis-enyl)-4-trimethylsiloxycyclopent-2-en-1-one | dl-11α,16-dihydroxy-9-oxo-16-methyl-19-chloro-2-nor-20-nor-5-cis-13-trans prostadienoic acid |
| 3 | 1-trans-iodo-4-methyl-7-chloro-1-heptene | 2-(5-carbotrimethylsiloxypent-2-cis-enyl)-4-trimethylsiloxycyclopent-2-en-1-one | dl-11α,16-dihydroxy-9-oxo-16-vinyl-19-chloro-2-nor-20-nor-5-cis-13-trans prostadienoic acid |
| 4 | 1-trans-iodo-4-vinyl-7-chloro-1-heptene | 2-(5-carbotrimethylsiloxypent-2-cis-enyl)-4-trimethylsiloxycyclopent-2-en-1-one | dl-11α,16-dihydroxy-9-oxo-16-ethynyl-19-chloro-2-nor-20-nor-5-cis-13-trans prostadienoic acid |
| 5 | 1-trans-iodo-4-trimethylsilylethynyl-7-chloro-1-heptene | 2-(5-carbotrimethylsiloxypent-2-cis-enyl)-4-trimethylsiloxycyclopent-2-en-1-one | dl-11α,16-dihydroxy-9-oxo-19-chloro-20-nor-5-cis-13-trans prostadienoic acid |
| 6 | 1-trans-iodo-7-chloro-1-heptene | 2-(6-carbotrimethylsiloxyhex-2-cis-enyl)-4-trimethylsiloxycyclopent-2-en-1-one | dl-11α,16-dihydroxy-9-oxo-16-methyl-19-chloro-20-nor-5-cis-13-trans prostadienoic acid |
| 7 | 4-triethylsiloxy-1-heptene | 2-(6-carbotrimethylsiloxyhex-2-cis-enyl)-4-trimethylsiloxycyclopent-2-en-1-one | dl-11α,16-dihydroxy-9-oxo-16-vinyl-19-chloro-20-nor-5-cis-13-trans prostadienoic acid |
| 8 | 1-trans-iodo-4-methyl-7-chloro-1-heptene | 2-(6-carbotrimethylsiloxyhex-2-cis-enyl)-4-trimethylsiloxycyclopent-2-en-1-one | dl-11α,16-dihydroxy-9-oxo-16-ethynyl-19-chloro-20-nor-5-cis-13-trans prostadienoic acid |
| 9 | 1-trans-iodo-4-vinyl-7-chloro-1-heptene | 2-(6-carbotrimethylsiloxyhex-2-cis-enyl)-4-trimethylsiloxycyclopent-2-en-1-one | dl-11α,16-dihydroxy-9-oxo-19-chloro-2-homo-20-nor-5-cis-13-trans prostadienoic acid |
| 10 | 1-trans-iodo-4-trimethylsilylethynyl-7-chloro-1-heptene | 2-(7-carbotrimethylsiloxyhept-2-cis-enyl)-4-trimethylsiloxycyclopent-2-en-1-one | dl-11α,16-dihydroxy-9-oxo-16-methyl-19-chloro-2-homo-20-nor-5-cis-13-trans prostadienoic acid |
| 11 | 1-trans-iodo-7-chloro-1-heptene | 2-(7-carbotrimethylsiloxyhept-2-cis-enyl)-4-trimethylsiloxycyclopent-2-en-1-one | dl-11α,16-dihydroxy-9-oxo-16-vinyl-19-chloro-2-homo-20-nor-5-cis-13-trans prostadienoic acid |
| 12 | 4-triethylsiloxy-1-heptene | 2-(7-carbotrimethylsiloxyhept-2-cis-enyl)-4-trimethylsiloxycyclopent-2-en-1-one | dl-11α,16-dihydroxy-9-oxo-16-ethynyl-19-chloro-2-homo-20-nor-5-cis-13-trans prostadienoic acid |
| 13 | 1-trans-iodo-4-methyl-7-chloro-1-heptene | 2-(6-carbotrimethylsiloxyhex-2-cis-enyl)-4-trimethylsiloxycyclopent-2-en-1-one | nat-11α,16-dihydroxy-9-oxo-19-chloro-20-nor-5-cis-13-trans prostadienoic acid |
| 14 | 1-trans-iodo-4-vinyl-7-chloro-1-heptene | 2-(6-carbotrimethylsiloxyhex-2-cis-enyl)-4-trimethylsiloxycyclopent-2-en-1-one | nat-11α,16-dihydroxy-9-oxo-16-methyl-19-chloro-20-nor-5-cis-13-trans prostadienoic acid |
| 15 | 4-trimethylsiloxy-1-heptene | 2-(6-carbotrimethylsiloxyhex-2-cis-enyl)-4-trimethylsiloxycyclopent-2-en-1-one | nat-11α,16-dihydroxy-9-oxo-16-vinyl-19-chloro-20-nor-5-cis-13-trans prostadienoic acid |
| 16 | 1-trans-iodo-4-trimethylsilylethynyl-7-chloro-1-heptene | 2-(6-carbotrimethylsiloxyhex-2-cis-enyl)-4-trimethylsiloxycyclopent-2-en-1-one | nat-11,16-dihydroxy-9-oxo-16-ethynyl-19-chloro-20-nor-5-cis-13-trans prostadienoic acid |

| EXAMPLE | VINYL IODIDE | CYCLOPENTENONE | PRODUCT PROSTAGLANDIN OF THE 11-DEOXY PGE2 SERIES |
|---|---|---|---|
| 17 | 1-trans-iodo-7-chloro-1-heptene | 2-(5-carboethoxypent-2-cis-enyl) cyclopent-2-en-1-one | dl-16-hydroxy-9-oxo-19-chloro-2-nor-20-nor-5-cis-13-trans prostadienoic acid |
| 18 | 4-triethylsiloxy-1-heptene | 2-(5-carboethoxypent-2-cis-enyl) cyclopent-2-en-1-one | dl-16-hydroxy-9-oxo-16-methyl-19-chloro-2-nor-20-nor-5-cis-13-trans prostadienoic acid |
| 19 | 1-trans-iodo-4-methyl-7-chloro-1-heptene | 2-(5-carboethoxypent-2-cis-enyl) cyclopent-2-en-1-one | dl-16-hydroxy-9-oxo-16-vinyl-19-chloro-2-nor-20-nor-5-cis-13-trans prostadienoic acid |
| 20 | 1-trans-iodo-4-vinyl-7-chloro-1-heptene | 2-(5-carboethoxypent-2-cis-enyl) cyclopent-2-en-1-one | dl-16-hydroxy-9-oxo-16-ethynyl-19-chloro-2-nor-20-nor-5-cis-13-trans prostadienoic acid |
| 21 | 1-trans-iodo-4-trimethylsilylethynyl-7-chloro-1-heptene | 2-(5-carboethoxypent-2-cis-enyl) cyclopent-2-en-1-one | dl-16-hydroxy-9-oxo-19-chloro-20-nor-5-cis-13-trans prostadienoic acid |
| 22 | 1-trans-iodo-7-chloro-1-heptene | 2-(6-carboethoxyhex-2-cis-enyl) cyclopent-2-en-1-one | dl-16-hydroxy-9-oxo-16-methyl-19-chloro-20-nor-5-cis-13-trans prostadienoic acid |
| 23 | 4-trimethylsiloxy-1-heptene | 2-(6-carboethoxyhex-2-cis-enyl) cyclopent-2-en-1-one | dl-16-hydroxy-9-oxo-16-vinyl-19-chloro-20-nor-5-cis-13-trans prostadienoic acid |
| 24 | 1-trans-iodo-4-trimethylsilylethynyl-7-chloro-1-heptene | 2-(6-carboethoxyhex-2-cis-enyl) cyclopent-2-en-1-one | dl-16-hydroxy-9-oxo-16-ethynyl-19-chloro-20-nor-5-cis-13-trans prostadienoic acid |
| 25 | 1-trans-iodo-7-chloro-1-heptene | 2-(7-carboethoxyhept-2-cis-enyl) cyclopent-2-en-1-one | dl-16-hydroxy-9-oxo-19-chloro-2-homo-20-nor-5-cis-13-trans prostadienoic acid |
| | 4-triethylsiloxy-1-heptene | | |

| | | -continued | |
|---|---|---|---|
| 26 | 1-trans-iodo-4-methyl-7-chloro-4-trimethylsiloxy-1-heptene | 2-(7-carboethoxyhept-2-cis-enyl)cyclopent-2-en-1-one | dl-16-hydroxy-9-oxo-16-methyl-19-chloro-2-homo-20-nor-5-cis-13-trans prostadienoic acid |
| 27 | 1-trans-iodo-4-vinyl-7-chloro-4-trimethylsiloxy-1-heptene | 2-(7-carboethoxyhept-2-cis-enyl)cyclopent-2-en-1-one | dl-16-hydroxy-9-oxo-16-vinyl-19-chloro-2-homo-20-nor-5-cis-13-trans prostadienoic acid |
| 28 | 1-trans-iodo-4-trimethylsilylethynyl-7-chloro-4-trimethylsiloxy-1-heptene | 2-(7-carboethoxyhept-2-cis-enyl)cyclopent-2-en-1-one | dl-16-hydroxy-9-oxo-16-ethynyl-19-chloro-2-homo-20-nor-5-cis-13-trans prostadienoic acid |

Treatment of the $PGE_2$ derivatives of Examples of Table II with lithium perhydro-9β-boraphenalyl hydride by the procedure of Reference Example 6 is productive of the $PGF_{2\alpha}$ derivatives of Examples 29–56 of Table II.

| EXAMPLE | STARTING PROSTAGLANDIN OF THE PGE SERIES | PRODUCT PROSTAGLANDIN OF THE $PGE_{2\alpha}$ SERIES |
|---|---|---|
| 29 | dl-11α,16-dihydroxy-9-oxo-19-chloro-2-nor-20-nor-5-cis-13-trans prostadienoic acid | dl-9α,11α,16-trihydroxy-19-chloro-2-nor-20-nor-5-cis-13-trans prostadienoic acid |
| 30 | dl-11α,16-dihydroxy-9-oxo-16-methyl-19-chloro-2-nor-20-nor-5-cis-13-trans prostadienoic acid | dl-9α,11α,16-trihydroxy-16-methyl-19-chloro-2-nor-20-nor-5-cis-13-trans prostadienoic acid |
| 31 | dl-11α,16-dihydroxy-9-oxo-16-vinyl-19-chloro-2-nor-20-nor-5-cis-13-trans prostadienoic acid | dl-9α,11α,16-trihydroxy-16-vinyl-19-chloro-2-nor-20-nor-5-cis-13-trans prostadienoic acid |
| 32 | dl-11α,16-dihydroxy-9-oxo-16-ethynyl-19-chloro-2-nor-20-nor-5-cis-13-trans prostadienoic acid | dl-9α,11α,16-trihydroxy-16-ethynyl-19-chloro-2-nor-20-nor-5-cis-13-trans prostadienoic acid |
| 37 | dl-11α,16-dihydroxy-9-oxo-19-chloro-2-homo-20-nor-5-cis-13-trans prostadienoic acid | dl-9α,11α,16-trihydroxy-19-chloro-2-homo-20-nor-5-cis-13-trans prostadienoic acid |
| 38 | dl-11α,16-dihydroxy-9-oxo-16-methyl-19-chloro-2-nor-20-nor-5-cis-13-trans prostadienoic acid | dl-9α,11α,16-trihydroxy-16-methyl-19-chloro-2-homo-20-nor-5-cis-13-trans prostadienoic acid |
| 39 | dl-11α,16-dihydroxy-9-oxo-16-vinyl-19-chloro-2-homo-20-nor-5-cis-13-trans prostadienoic acid | dl-9α,11α,16-trihydroxy-16-vinyl-19-chloro-2-homo-20-nor-5-cis-13-trans prostadienoic acid |
| 40 | dl-11α,16-dihydroxy-9-oxo-16-ethynyl-19-chloro-2-homo-20-nor-5-cis-13-trans prostadienoic acid | dl-9α,11α,16-trihydroxy-16-ethynyl-19-chloro-2-homo-20-nor-5-cis-13-trans prostadienoic acid |
| 41 | nat-11α,16-dihydroxy-9-oxo-19-chloro-20-nor-5-cis-13-trans prostadienoic acid | nat-9α,11α,16-trihydroxy-19-chloro-20-nor-5-cis-13-trans prostadienoic acid |
| 42 | nat-11α,16-dihydroxy-9-oxo-16-methyl-19-chloro-20-nor-5-cis-13-trans prostadienoic acid | nat-9α,11α,16-trihydroxy-16-methyl-19-chloro-20-nor-5-cis-13-trans prostadienoic acid |
| 43 | nat-11α,16-dihydroxy-9-oxo-16-vinyl-19-chloro-20-nor-5-cis-13-trans prostadienoic acid | dl-9α,11α,16-trihydroxy-16-vinyl-19-chloro-20-nor-5-cis-13-trans prostadienoic acid |
| 44 | nat-11α,16-dihydroxy-9-oxo-16-ethynyl-19-chloro-20-nor-5-cis-13-trans prostadienoic acid | nat-9α,11α,16-trihydroxy-16-ethynyl-19-chloro-20-nor-5-cis-13-trans prostadienoic acid |

| EXAMPLE | STARTING PROSTAGLANDIN OF THE PGE SERIES | PRODUCT PROSTAGLANDIN OF THE 11-DEOXY $FGF_{2\alpha}$ SERIES |
|---|---|---|
| 45 | dl-16-hydroxy-9-oxo-19-chloro-2-nor-20-nor-5-cis-13-trans prostadienoic acid | dl-9α,16-dihydroxy-19-chloro-2-nor-20-nor-5-cis-13-trans prostadienoic acid |
| 46 | dl-16-hydroxy-9-oxo-16-methyl-19-chloro-2-nor-20-nor-5-cis-13-trans prostadienoic acid | dl-9α,16-dihydroxy-16-methyl-19-chloro-2-nor-20-nor-5-cis-13-trans prostadienoic acid |
| 47 | dl-16-hydroxy-9-oxo-16-vinyl-19-chloro-2-nor-20-nor-5-cis-13-trans prostadienoic acid | dl-9α,16-dihydroxy-16-vinyl-19-chloro-2-nor-20-nor-5-cis-13-trans prostadienoic acid |
| 48 | dl-16-hydroxy-9-oxo-16-ethynyl-19-chloro-2-nor-20-nor-5-cis-13-trans prostadienoic acid | dl-9α,16-dihydroxy-16-ethynyl-19-chloro-2-nor-20-nor-5-cis-13-trans prostadienoic acid |
| 49 | dl-16-hydroxy-9-oxo-19-chloro-20-nor-5-cis-13-trans prostadienoic acid | dl-9α,16-dihydroxy-19-chloro-20-nor-5-cis-13-trans prostadienoic acid |
| 50 | dl-16-hydroxy-9-oxo-16-methyl-19-chloro-20-nor-5-cis-13-trans prostadienoic acid | dl-9α,16-dihydroxy-16-methyl-19-chloro-20-nor-5-cis-13-trans prostadienoic acid |
| 51 | dl-16-hydroxy-9-oxo-16-vinyl-19-chloro-20-nor-5-cis-13-trans prostadienoic acid | dl-9α,16-dihydroxy-16-vinyl-19-chloro-20-nor-5-cis-13-trans prostadienoic acid |
| 52 | dl-16-hydroxy-9-oxo-16-ethynyl-19-chloro-20-nor-5-cis-13-trans prostadienoic acid | dl-9α,16-dihydroxy-16-ethynyl-19-chloro-20-nor-5-cis-13-trans prostadienoic acid |
| 53 | dl-16-hydroxy-9-oxo-19-chloro-2-homo-20-nor-5-cis-13-trans prostadienoic acid | dl-9α,16-dihydroxy-19-chloro-2-homo-20-nor-5-cis-13-trans prostadienoic acid |
| 54 | dl-16-hydroxy-9-oxo-16-methyl-19-chloro-2-homo-20-nor-5-cis-13-trans prostadienoic acid | dl-9α,16-dihydroxy-16-methyl-19-chloro-2-homo-20-nor-5-cis-13-trans prostadienoic acid |
| 55 | dl-16-hydroxy-9-oxo-16-vinyl-19-chloro-2-homo-20-nor-5-cis-13-trans prostadienoic acid | dl-9α,16-dihydroxy-16-vinyl-19-chloro-2-homo-20-nor-5-cis-13-trans prostadienoic acid |
| 56 | dl-16-hydroxy-9-oxo-16-ethynyl-19-chloro-2-homo-20-nor-5-cis-13-trans prostadienoic acid | dl-9α,16-dihydroxy-16-ethynyl-19-chloro-2-homo-20-nor-5-cis-13-trans prostadienoic acid |

| EXAMPLE | STARTING PROSTAGLANDIN OF THE PGE SERIES | PRODUCT PROSTAGLANDIN OF THE $PGF_{2\beta}$ SERIES |
|---|---|---|
| 57 | dl-11α,16-dihydroxy-9-oxo-19-chloro-2-nor-20-nor-5-cis-13-trans prostadienoic acid | dl-9β,11α,16-trihydroxy-19-chloro-2-nor-20-nor-5-cis-13-trans prostadienoic acid |
| 58 | dl-11α,16-dihydroxy-9-oxo-16-methyl-19-chloro-2-nor-20-nor-5-cis-13-trans prostadienoic acid | dl-9β,11α,16-trihydroxy-16-methyl-19-chloro-2-nor-20-nor-5-cis-13-trans prostadienoic acid |
| 59 | dl-11α,16-dihydroxy-9-oxo-16-vinyl-19-chloro-2-nor-20-nor-5-cis-13-trans prostadienoic acid | dl-9β,11α,16-trihydroxy-16-vinyl-19-chloro-2-nor-20-nor-5-cis-13-trans prostadienoic acid |
| 60 | dl-11α,16-dihydroxy-9-oxo-16-ethynyl-19-chloro-2-nor-20-nor-5-cis-13-trans prostadienoic acid | dl-9β,11α,16-trihydroxy-16-ethynyl-19-chloro-2-nor-20-nor-5-cis-13-trans prostadienoic acid |
| 61 | dl-11α,16-dihydroxy-9-oxo-19-chloro-20-nor-5-cis-13-trans prostadienoic acid | dl-9β,11α,16-trihydroxy-19-chloro-20-nor-5-cis-13-trans prostadienoic acid |
| 62 | dl-11α,16-dihydroxy-9-oxo-16-methyl-19-chloro-20-nor-5-cis-13-trans prostadienoic acid | dl-9β,11α,16-trihydroxy-16-methyl-19-chloro-20-nor-5-cis-13-trans prostadienoic acid |
| 63 | dl-11α,16-dihydroxy-9-oxo-16-vinyl-19-chloro-20-nor-5-cis-13-trans prostadienoic acid | dl-9β,11α,16-trihydroxy-16-vinyl-19-chloro-20-nor-5-cis-13-trans prostadienoic acid |
| 64 | dl-11α,16-dihydroxy-9-oxo-16-ethynyl-19-chloro-20-nor-5-cis-13-trans prostadienoic acid | dl-9β,11α,16-trihydroxy-16-ethynyl-19-chloro-20-nor-5-cis-13-trans prostadienoic acid |
| 65 | dl-11α,16-dihydroxy-9-oxo-19-chloro-2-homo-20-nor-5-cis-13-trans prostadienoic acid | dl-9β,11α,16-trihydroxy-19-chloro-2-homo-20-nor-5-cis-13-trans prostadienoic acid |
| 66 | dl-11α,16-dihydroxy-9-oxo-16-methyl-19-chloro- | dl-9β,11α,16-trihydroxy-16-methyl-19-chloro- |

-continued

| | | |
|---|---|---|
| 67 | dl-11α,16-dihydroxy-9-oxo-16-vinyl-19-chloro-2-homo-20-nor-5-cis-13-trans prostadienoic acid | dl-9β,11α,16-trihydroxy-16-vinyl-19-chloro-2-homo-20-nor-5-cis-13-trans prostadienoic acid |
| 68 | dl-11α,16-dihydroxy-9-oxo-16-ethynyl-19-chloro-2-homo-20-nor-5-cis-13-trans prostadienoic acid | dl-9β,11α,16-trihydroxy-16-ethynyl-19-chloro-2-homo-20-nor-5-cis-13-trans prostadienoic acid |
| 69 | nat-11α,16-dihydroxy-9-oxo-19-chloro-20-nor-5-cis-13-trans prostadienoic acid | nat-9β,11α,16-trihydroxy-19-chloro-20-nor-5-cis-13-trans prostadienoic acid |
| 70 | nat-11α,16-dihydroxy-9-oxo-16-methyl-19-chloro-20-nor-5-cis-13-trans prostadienoic acid | nat-9β,11α,16-trihydroxy-16-methyl-19-chloro-20-nor-5-cis-13-trans prostadienoic acid |
| 71 | nat-11α,16-dihydroxy-9-oxo-16-vinyl-19-chloro-20-nor-5-cis-13-trans prostadienoic acid | nat-9β,11α,16-trihydroxy-16-vinyl-19-chloro-20-nor-5-cis-13-trans prostadienoic acid |
| 72 | nat-11α,16-dihydroxy-9-oxo-16-ethynyl-19-chloro-20-nor-5-cis-13-trans prostadienoic acid | nat-9β,11α,16-trihydroxy-16-ethynyl-19-chloro-20-nor-5-cis-13-trans prostadienoic acid |

| EXAMPLE | STARTING PROSTAGLANDIN OF THE PGE SERIES | PRODUCT PROSTAGLANDIN OF THE 11-DEOXY PGF2β SERIES |
|---|---|---|
| 73 | dl-16-hydroxy-9-oxo-19-chloro-2-nor-20-nor-5-cis-13-trans prostadienoic acid | dl-9β,16-dihydroxy-19-chloro-2-nor-20-nor-5-cis-13-trans prostadienoic acid |
| 74 | dl-16-hydroxy-9-oxo-16-methyl-19-chloro-2-nor-20-nor-5-cis-13-trans prostadienoic acid | dl-9β,16-dihydroxy-16-methyl-19-chloro-2-nor-20-nor-5-cis-13-trans prostadienoic acid |
| 75 | dl-16-hydroxy-9-oxo-16-vinyl-19-chloro-2-nor-20-nor-5-cis-13-trans prostadienoic acid | dl-9β,16-dihydroxy-16-vinyl-19-chloro-2-nor-20-nor-5-cis-13-trans prostadienoic acid |
| 76 | dl-16-hydroxy-9-oxo-16-ethynyl-19-chloro-2-nor-20-nor-5-cis-13-trans prostadienoic acid | dl-9β,16-dihydroxy-16-ethynyl-19-chloro-2-nor-20-nor-5-cis-13-trans prostadienoic acid |
| 77 | dl-16-hydroxy-9-oxo-19-chloro-20-nor-5-cis-13-trans prostadienoic acid | dl-9β,16-dihydroxy-19-chloro-20-nor-5-cis-13-trans prostadienoic acid |
| 78 | dl-16-hydroxy-9-oxo-16-methyl-19-chloro-20-nor-5-cis-13-trans prostadienoic acid | dl-9β,16-dihydroxy-16-methyl-19-chloro-20-nor-5-cis-13-trans prostadienoic acid |
| 79 | dl-16-hydroxy-9-oxo-16-vinyl-19-chloro-20-nor-5-cis-13-trans prostadienoic acid | dl-9β,16-dihydroxy-16-vinyl-19-chloro-20-nor-5-cis-13-trans prostadienoic acid |
| 80 | dl-16-hydroxy-9-oxo-16-ethynyl-19-chloro-20-nor-5-cis-13-trans prostadienoic acid | dl-9β,16-dihydroxy-16-ethynyl-19-chloro-20-nor-5-cis-13-trans prostadienoic acid |
| 81 | dl-16-hydroxy-9-oxo-19-chloro-2-homo-20-nor-5-cis-13-trans prostadienoic acid | dl-9β,16-dihydroxy-19-chloro-2-homo-20-nor-5-cis-13-trans prostadienoic acid |
| 82 | dl-16-hydroxy-9-oxo-16-methyl-19-chloro-2-homo-20-nor-5-cis-13-trans prostadienoic acid | dl-9β,16-dihydroxy-16-methyl-19-chloro-2-homo-20-nor-5-cis-13-trans prostadienoic acid |
| 83 | dl-16-hydroxy-9-oxo-16-vinyl-19-chloro-2-homo-20-nor-5-cis-13-trans prostadienoic acid | dl-9β,16-dihydroxy-16-vinyl-19-chloro-2-homo-20-nor-5-cis-13-trans prostadienoic acid |
| 84 | dl-16-hydroxy-9-oxo-16-ethynyl-19-chloro-2-homo-20-nor-5-cis-13-trans prostadienoic acid | dl-9β,16-dihydroxy-16-ethynyl-19-chloro-2-homo-20-nor-5-cis-13-trans prostadienoic acid |

Treatment of the PGE$_2$ derivatives of Examples 1–28 of Table II with sodium borohydride by the procedure of Reference Example 7 is productive of the PGFα and PGFβ derivatives of Examples 57 to 84 of Table II.

While specific embodiments of this invention have been described with particularity herein, it will be understood that the invention embraces all changes and modifications of the particular compounds chosen for purposes of illustration herein which do not depart from the spirit and scope of the invention.

I claim:

1. An optically active compound of the formula:

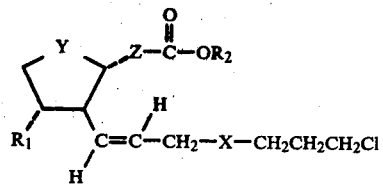

wherein
X is:

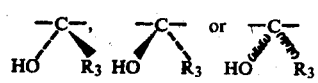

and
Y is

$R_1$ is selected from the group consisting of hydrogen and hydroxyl;

$R_2$ is selected from the group consisting of hydrogen and $C_1$ to $C_6$ alkyl;

$R_3$ is selected from the group consisting of hydrogen, methyl, vinyl and ethynyl;

Z is

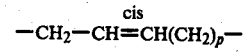

wherein p is 2 to 5, the racemic mixture thereof, and when $R_2$ is hydrogen, the pharmaceutically acceptable salts thereof.

2. The compound according to claim 1, wherein $R_1$ is hydroxyl.

3. The compound according to claim 1, wherein $R_3$ is hydrogen.

4. The compound according to claim 1, wherein $R_3$ is methyl.

5. The compound according to claim 1, wherein $R_3$ is vinyl or ethynyl.

6. The racemic compounds according to claim 3, 11α,16α/β-dihydroxy-9-oxo-19-chloro-20-nor-5-cis,13-trans-prostadienoic acid, the individual 16α- and 16β-hydroxy racemates and the methyl esters thereof.

7. The optically active compounds according to claim 3, nat.-11α,16α/β-dihydroxy-9-oxo-19-chloro-20-nor-5-cis,13-trans-prostadienoic acid, the individual 16α- and 16β-hydroxy isomers and the methyl esters thereof.

8. The racemic compounds according to claim 4, 11α,16α/β-dihydroxy-9-oxo-16-methyl-19-chloro-20-nor-5-cis,13-trans-prostadienoic acid, the individual 16α- and 16β-hydroxy racemates, and the methyl esters thereof.

9. The optically active compounds according to claim 4, 11α,16α/β-dihydroxy-9-oxo-16-methyl-19-chloro-20-nor-5-cis,13-trans-propstadienoic acid, the individual 16α- and 16β-hydroxy isomers, and the methyl esters thereof.

10. The racemic compounds according to claim 5, 11α,16α/β-dihydroxy-9-oxo-16-vinyl-19-chloro-20-nor-5-cis,13-trans-prostadienoic acid, the individual 16α- and 16β-hydroxy racemates, and the methyl esters thereof.

11. The optically active compounds according to claim 5, nat.-11α,16α/β-dihydroxy-9-oxo-16-vinyl-19-chloro-20-nor-5-cis,13-trans-prostadienoic acid, the individual 16α- and 16β-hydroxy isomers, and the methyl esters thereof.

12. The racemic compounds according to claim 5, 11α,16α/β-dihydroxy-9-oxo-16-ethynyl-19-chloro-20-nor-5-cis,13-trans-prostadienoic acid, the individual 16α- and 16β-hydroxy racemates, and the methyl esters thereof.

13. The optically active compounds according to claim 5, nat.11α,16α/β-dihydroxy-9-oxo-16-ethynyl-19-chloro-20-nor-5-cis,13-trans-prostadienoic acid, the individual 16α- and 16β-hydroxy isomers, and the methyl esters thereof.

14. The optically active compound according to claim 11, nat.-11α,16α-dihydroxy-9-oxo-16-vinyl-19-chloro-20-nor-5-cis,13-trans-prostadienoic acid, methyl ester.

* * * * *